(12) United States Patent
O'Keefe et al.

(10) Patent No.: US 10,974,023 B2
(45) Date of Patent: Apr. 13, 2021

(54) MEDICAL TUBE CLEARANCE

(71) Applicant: CLEARFLOW, INC., Irvine, CA (US)

(72) Inventors: Kathryn Bernadine O'Keefe, Bend, OR (US); Stephen Riddle McDaniel, San Francisco, CA (US); Edward M. Boyle, Jr., Bend, OR (US); Kenneth Allan Beres, Studio City, CA (US); Kenneth J. Chesnin, Long Beach, CA (US)

(73) Assignee: CLEARFLOW, INC., Irvine, CA (US)

( * ) Notice: Subject to any disclaimer, the term of this patent is extended or adjusted under 35 U.S.C. 154(b) by 385 days.

(21) Appl. No.: 14/624,328

(22) Filed: Feb. 17, 2015

(65) Prior Publication Data
US 2015/0231361 A1 Aug. 20, 2015

Related U.S. Application Data

(60) Provisional application No. 61/940,725, filed on Feb. 17, 2014.

(51) Int. Cl.
*A61M 25/00* (2006.01)
*A61M 1/00* (2006.01)

(52) U.S. Cl.
CPC ........ *A61M 25/0026* (2013.01); *A61M 1/008* (2013.01); *A61M 25/00* (2013.01);
(Continued)

(58) Field of Classification Search
CPC ............ A61M 25/0026; A61M 1/0058; A61M 1/008; A61M 27/00; A61B 90/70;
(Continued)

(56) References Cited

U.S. PATENT DOCUMENTS

| 341,653 A | 12/1968 | Richard et al. |
|---|---|---|
| 3,416,532 A | 12/1968 | Grossman |

(Continued)

FOREIGN PATENT DOCUMENTS

| CN | 201768722 U | 3/2011 |
|---|---|---|
| DE | 202009006908 U1 | 11/2010 |

(Continued)

OTHER PUBLICATIONS

See attached translation of Gefner (DE 10 2010 026 774).*

(Continued)

*Primary Examiner* — Nathan R Price
*Assistant Examiner* — Courtney B Frederickson
(74) *Attorney, Agent, or Firm* — Pearne & Gordon LLP

(57) ABSTRACT

A device for clearing obstructions from a medical tube, such as a chest tube, is disclosed in various embodiments. In embodiments, the device features a clearance member that is formed to match a cross-section of a medical tube. Still further, the clearance member can have a plurality of branches, each branch configured to clear a respective lumen in a partitioned region of a medical tube. In this manner, the clearance member may clear obstructions from individual lumens of the partitioned region of the medical tube. Device for actuating a clearance member to clear obstructions within a medical tube are also disclosed. Methods of clearing a medical tube of obstructions are also disclosed.

23 Claims, 18 Drawing Sheets

(52) U.S. Cl.
CPC . *A61M 2025/0019* (2013.01); *A61M 2209/10* (2013.01); *A61M 2210/101* (2013.01)

(58) Field of Classification Search
CPC ..... A61B 2090/701; A61B 1/122; B08B 9/02; B08B 9/04
See application file for complete search history.

(56) References Cited

U.S. PATENT DOCUMENTS

| | | | |
|---|---|---|---|
| 3,946,741 A | 3/1976 | Adair | |
| 3,957,054 A | 5/1976 | McFarlane | |
| 3,991,762 A | 11/1976 | Radford | |
| 4,006,743 A | 2/1977 | Kowarski | |
| 4,056,104 A | 11/1977 | Jaffe | |
| 4,148,319 A | 4/1979 | Kasper et al. | |
| 4,228,802 A | 10/1980 | Trott | |
| 4,257,422 A | 3/1981 | Duncan | |
| 4,317,452 A | 3/1982 | Russo et al. | |
| 4,324,262 A | 4/1982 | Hall | |
| 4,398,910 A | 8/1983 | Blake et al. | |
| 4,429,693 A | 2/1984 | Blake et al. | |
| 4,445,897 A * | 5/1984 | Ekbladh | A61M 27/00 604/43 |
| 4,465,481 A | 8/1984 | Blake | |
| 4,523,920 A | 6/1985 | Russo | |
| 4,546,519 A | 10/1985 | Pembroke | |
| 4,569,344 A | 2/1986 | Palmer | |
| 4,628,928 A | 12/1986 | Lowell | |
| 4,638,539 A | 1/1987 | Palmer | |
| 4,692,153 A | 9/1987 | Berlin et al. | |
| 4,696,296 A | 9/1987 | Palmer | |
| 4,698,058 A | 10/1987 | Greenfeld et al. | |
| 4,706,671 A | 11/1987 | Weinrib | |
| 4,723,549 A | 2/1988 | Wholey et al. | |
| 4,728,319 A | 2/1988 | Masch | |
| 4,762,125 A | 8/1988 | Leiman et al. | |
| 4,771,772 A | 9/1988 | DeWitt | |
| 4,781,678 A | 11/1988 | de Couet et al. | |
| 4,865,030 A | 9/1989 | Polyak | |
| 4,865,586 A | 9/1989 | Hedberg | |
| 4,889,106 A | 12/1989 | Watanabe | |
| 4,909,781 A | 3/1990 | Husted | |
| 4,921,488 A | 5/1990 | Maitz et al. | |
| 4,950,232 A | 8/1990 | Ruzicka et al. | |
| 4,967,743 A | 11/1990 | Lambert | |
| 5,003,657 A | 4/1991 | Boiteau et al. | |
| 5,009,659 A | 4/1991 | Hamlin et al. | |
| 5,062,835 A | 4/1991 | Maitz et al. | |
| 5,073,164 A | 12/1991 | Hollister et al. | |
| D328,790 S | 8/1992 | Herweck et al. | |
| 5,141,503 A | 8/1992 | Sewell, Jr. | |
| 5,188,618 A | 2/1993 | Thomas | |
| 5,215,522 A | 6/1993 | Page et al. | |
| 5,240,675 A | 8/1993 | Wilk et al. | |
| D340,285 S | 10/1993 | Herweck et al. | |
| 5,251,356 A | 10/1993 | Oaki et al. | |
| 5,260,020 A | 11/1993 | Wilk et al. | |
| 5,261,877 A | 11/1993 | Fine et al. | |
| 5,297,310 A | 3/1994 | Cox et al. | |
| 5,336,177 A | 8/1994 | Marcus | |
| 5,349,950 A | 9/1994 | Ulrich et al. | |
| 5,370,610 A * | 12/1994 | Reynolds | A61M 25/003 604/43 |
| 5,490,503 A | 2/1996 | Hollister | |
| 5,505,713 A | 4/1996 | Van Antwerp | |
| 5,514,112 A | 5/1996 | Chu et al. | |
| 5,520,635 A | 5/1996 | Gelbfish | |
| 5,522,801 A | 6/1996 | Wang | |
| 5,536,248 A | 7/1996 | Weaver et al. | |
| 5,538,511 A | 7/1996 | Van Antwerp | |
| 5,599,299 A | 2/1997 | Weaver et al. | |
| 5,599,300 A | 2/1997 | Weaver et al. | |
| 5,630,823 A | 5/1997 | Schmitz-Rode et al. | |
| 5,653,696 A | 8/1997 | Shiber | |
| 5,688,234 A | 11/1997 | Frisbie | |
| 5,693,011 A | 12/1997 | Onik | |
| 5,715,815 A | 2/1998 | Lorenzen et al. | |
| 5,768,741 A * | 6/1998 | Leiman | B08B 9/00 15/104.05 |
| 5,772,261 A | 6/1998 | Magram | |
| 5,788,678 A | 8/1998 | Van Antwerp | |
| 5,788,681 A | 8/1998 | Weaver et al. | |
| 5,788,710 A | 8/1998 | Bates et al. | |
| 5,807,330 A | 9/1998 | Teitelbaum | |
| 5,830,127 A | 11/1998 | DeCastro | |
| 5,843,028 A | 12/1998 | Weaver et al. | |
| 5,868,720 A | 2/1999 | Van Antwerp | |
| 5,895,398 A | 4/1999 | Wensel et al. | |
| 5,897,534 A | 4/1999 | Heim et al. | |
| 5,902,314 A | 5/1999 | Koch | |
| 5,911,710 A | 6/1999 | Barry et al. | |
| 5,911,734 A | 6/1999 | Tsugita et al. | |
| 5,913,852 A | 6/1999 | Magram | |
| 5,921,952 A | 7/1999 | Desmond, III et al. | |
| 5,928,218 A | 7/1999 | Gelbfish | |
| 5,931,821 A | 8/1999 | Weilbacher et al. | |
| 5,957,932 A | 9/1999 | Bates et al. | |
| 5,964,004 A | 10/1999 | Bean | |
| 5,964,223 A | 10/1999 | Baran | |
| 5,989,241 A | 11/1999 | Plishka et al. | |
| 6,045,623 A | 4/2000 | Cannon | |
| 6,080,170 A | 6/2000 | Nash et al. | |
| 6,082,361 A | 7/2000 | Morejon | |
| 6,129,697 A | 10/2000 | Drasler et al. | |
| 6,168,603 B1 | 1/2001 | Leslie et al. | |
| 6,183,450 B1 | 2/2001 | Lois | |
| 6,248,100 B1 | 6/2001 | de Toledo et al. | |
| 6,264,624 B1 | 7/2001 | Desmond, III et al. | |
| 6,299,604 B1 | 10/2001 | Ragheb et al. | |
| 6,383,196 B1 | 5/2002 | Leslie et al. | |
| 6,436,112 B2 | 8/2002 | Wensel et al. | |
| 6,454,775 B1 | 9/2002 | Demarais et al. | |
| 6,485,497 B2 | 11/2002 | Wensel et al. | |
| 6,508,789 B1 | 1/2003 | Sinnott et al. | |
| 6,514,273 B1 | 2/2003 | Voss et al. | |
| 6,530,935 B2 | 3/2003 | Wensel et al. | |
| 6,547,761 B2 | 4/2003 | Liu | |
| 6,562,024 B2 | 5/2003 | Alvarez de Toledo et al. | |
| 6,582,400 B1 | 6/2003 | Hawk et al. | |
| 6,629,956 B1 | 10/2003 | Polidoro et al. | |
| 6,638,253 B2 | 10/2003 | Breznock | |
| 6,660,014 B2 | 12/2003 | Demarais et al. | |
| 6,663,650 B2 | 12/2003 | Sepetka et al. | |
| 6,679,262 B1 | 1/2004 | Morejon | |
| 6,692,459 B2 | 2/2004 | Teitelbaum | |
| 6,692,508 B2 | 2/2004 | Wensel et al. | |
| 6,692,509 B2 | 2/2004 | Wensel et al. | |
| 6,699,331 B1 | 3/2004 | Kritzler | |
| 6,702,830 B1 | 3/2004 | Demarais et al. | |
| 6,730,104 B1 | 5/2004 | Sepetka et al. | |
| 6,740,096 B2 | 5/2004 | Teague et al. | |
| 6,767,338 B2 | 7/2004 | Hawk et al. | |
| 6,780,193 B2 | 8/2004 | Leslie et al. | |
| 6,783,536 B2 | 8/2004 | Vilsmeier et al. | |
| 6,824,545 B2 | 11/2004 | Sepetka et al. | |
| 6,849,061 B2 | 2/2005 | Wagner | |
| 6,866,657 B2 | 3/2005 | Shchervinsky | |
| 6,889,400 B2 | 5/2005 | Kawazoe et al. | |
| 6,893,418 B2 | 5/2005 | Liu | |
| 6,893,424 B2 | 5/2005 | Shchervinsky | |
| 6,902,550 B2 | 6/2005 | Want et al. | |
| 6,905,484 B2 | 6/2005 | Buckman et al. | |
| 6,920,662 B2 * | 7/2005 | Moore | B08B 9/00 15/104.16 |
| 6,945,977 B2 | 9/2005 | Demarais et al. | |
| 7,004,954 B1 | 2/2006 | Voss et al. | |
| 7,028,707 B2 | 4/2006 | Corbeil et al. | |
| 7,037,313 B2 | 5/2006 | Ahn et al. | |
| 7,101,380 B2 | 9/2006 | Khachin et al. | |
| 7,125,402 B1 | 10/2006 | Yarger | |
| 7,135,010 B2 | 11/2006 | Buckman et al. | |
| 7,141,038 B2 | 11/2006 | Whalen et al. | |
| 7,211,067 B2 | 5/2007 | Hawk et al. | |

(56) References Cited

U.S. PATENT DOCUMENTS

| | | | |
|---|---|---|---|
| 7,229,433 B2 | 6/2007 | Mullen | |
| 7,241,287 B2 | 7/2007 | Shehada et al. | |
| 7,241,299 B2 | 7/2007 | Gerard | |
| 7,244,251 B2 | 7/2007 | Shehada et al. | |
| 7,252,659 B2 | 8/2007 | Shehada et al. | |
| 7,264,616 B2 | 9/2007 | Shehada et al. | |
| 7,267,671 B2 | 9/2007 | Shehada | |
| 7,285,126 B2 | 10/2007 | Sepetka et al. | |
| 7,326,197 B2 | 2/2008 | Breznock et al. | |
| 7,338,478 B2 | 3/2008 | Leiboff | |
| 7,338,501 B2 | 3/2008 | Teague et al. | |
| 7,419,483 B2 | 9/2008 | Shehada | |
| 7,610,106 B2 | 10/2009 | Yacoubian | |
| 7,686,801 B2 | 3/2010 | Corbeil et al. | |
| 7,695,467 B2 | 4/2010 | Breznock et al. | |
| 7,780,639 B2 | 8/2010 | Van Lue | |
| 7,799,046 B2 | 9/2010 | White et al. | |
| 7,811,293 B2 | 10/2010 | Simpson et al. | |
| 7,854,728 B2 * | 12/2010 | Boyle, Jr. | A61M 27/00 15/104.16 |
| 7,867,241 B2 | 1/2011 | Brock et al. | |
| 7,951,243 B2 | 5/2011 | Boyle, Jr. et al. | |
| 7,992,561 B2 | 8/2011 | Baker, Jr. et al. | |
| 8,048,233 B2 | 11/2011 | Boyle, Jr. et al. | |
| 8,157,919 B2 | 4/2012 | Vazales et al. | |
| 8,246,752 B2 | 8/2012 | Boyle, Jr. | |
| 8,262,645 B2 | 9/2012 | Bagwell et al. | |
| 8,388,759 B2 | 3/2013 | Boyle, Jr. et al. | |
| 8,566,995 B2 | 10/2013 | Asano et al. | |
| 9,724,498 B2 | 8/2017 | Querol Garcia | |
| 2001/0018572 A1 | 8/2001 | Kinsey et al. | |
| 2002/0058915 A1 | 5/2002 | Wakabayashi | |
| 2002/0128601 A1 | 9/2002 | Reilly et al. | |
| 2003/0069551 A1 | 4/2003 | Bradley, III et al. | |
| 2003/0181876 A1 | 9/2003 | Ahn et al. | |
| 2003/0216760 A1 | 11/2003 | Welch et al. | |
| 2004/0006331 A1 * | 1/2004 | Shchervinsky | A61M 1/008 604/541 |
| 2004/0073243 A1 | 4/2004 | Sepetka et al. | |
| 2004/0078026 A1 | 4/2004 | Wagner | |
| 2004/0092956 A1 | 5/2004 | Liddicoat et al. | |
| 2004/0181191 A1 | 9/2004 | Teitelbaum | |
| 2004/0219028 A1 | 11/2004 | Demarais et al. | |
| 2004/0230132 A1 | 11/2004 | Shehada | |
| 2005/0033348 A1 | 2/2005 | Sepetka et al. | |
| 2005/0055033 A1 | 3/2005 | Leslie et al. | |
| 2005/0059995 A1 | 3/2005 | Sepetka et al. | |
| 2005/0085849 A1 | 4/2005 | Sepetka et al. | |
| 2005/0125024 A1 | 6/2005 | Sepetka et al. | |
| 2005/0154373 A1 | 7/2005 | Deutsch | |
| 2005/0171478 A1 | 8/2005 | Selmon et al. | |
| 2005/0171566 A1 | 8/2005 | Kanamaru | |
| 2005/0216030 A1 | 9/2005 | Sepetka et al. | |
| 2005/0216050 A1 | 9/2005 | Sepetka et al. | |
| 2005/0228363 A1 | 10/2005 | Leiboff | |
| 2005/0228417 A1 | 10/2005 | Teitelbaum et al. | |
| 2005/0288686 A1 | 12/2005 | Sepetka et al. | |
| 2006/0004404 A1 | 1/2006 | Khachin et al. | |
| 2006/0142697 A1 | 6/2006 | Hawk et al. | |
| 2006/0167416 A1 | 7/2006 | Mathis et al. | |
| 2006/0195069 A1 | 8/2006 | Opie et al. | |
| 2006/0195137 A1 | 8/2006 | Sepetka et al. | |
| 2006/0206097 A1 | 9/2006 | Breznock et al. | |
| 2006/0264974 A1 | 11/2006 | Khachin et al. | |
| 2006/0264988 A1 | 11/2006 | Boyle | |
| 2006/0276814 A1 | 12/2006 | Omata et al. | |
| 2007/0032779 A1 | 2/2007 | Accisano et al. | |
| 2007/0049904 A1 | 3/2007 | Deutsch | |
| 2007/0078389 A1 | 4/2007 | Whalen et al. | |
| 2007/0083189 A1 | 4/2007 | Lampropoulos et al. | |
| 2007/0135795 A1 | 6/2007 | De Paulis | |
| 2007/0149946 A1 | 6/2007 | Viswanathan et al. | |
| 2007/0179513 A1 | 8/2007 | Deutsch | |
| 2007/0198030 A1 | 8/2007 | Martin et al. | |
| 2007/0208371 A1 | 9/2007 | French et al. | |
| 2007/0288036 A1 | 12/2007 | Seshadri et al. | |
| 2008/0045881 A1 | 2/2008 | Teitelbaum et al. | |
| 2008/0051720 A1 | 2/2008 | Nash et al. | |
| 2008/0091146 A1 | 4/2008 | Solovay et al. | |
| 2008/0109032 A1 | 5/2008 | Sepetka et al. | |
| 2008/0119869 A1 | 5/2008 | Teague et al. | |
| 2008/0177276 A1 | 7/2008 | Teague et al. | |
| 2008/0177296 A1 | 7/2008 | Sepetka et al. | |
| 2008/0183197 A1 | 7/2008 | Sepetka et al. | |
| 2008/0183198 A1 | 7/2008 | Sepetka et al. | |
| 2008/0183205 A1 | 7/2008 | Sepetka et al. | |
| 2008/0188876 A1 | 8/2008 | Sepetka et al. | |
| 2008/0188885 A1 | 8/2008 | Sepetka et al. | |
| 2008/0215077 A1 | 9/2008 | Sepetka et al. | |
| 2008/0234706 A1 | 9/2008 | Sepetka et al. | |
| 2009/0000045 A1 | 1/2009 | Kanno et al. | |
| 2009/0048651 A1 | 2/2009 | Andino et al. | |
| 2009/0062772 A1 | 3/2009 | Wakeford et al. | |
| 2009/0157060 A1 | 6/2009 | Teague et al. | |
| 2009/0188531 A1 | 7/2009 | Boyle, Jr. et al. | |
| 2009/0264833 A1 * | 10/2009 | Boyle, Jr. | B08B 9/0436 604/257 |
| 2009/0326513 A1 | 12/2009 | Deutsch et al. | |
| 2011/0023888 A1 | 2/2011 | Vazales et al. | |
| 2011/0040285 A1 | 2/2011 | Boyle | |
| 2011/0098660 A1 | 4/2011 | Porreca, Jr. | |
| 2011/0106019 A1 | 5/2011 | Bagwell et al. | |
| 2011/0289705 A1 | 12/2011 | Asano et al. | |
| 2012/0285485 A1 | 11/2012 | Majeed | |
| 2013/0018304 A1 | 1/2013 | Bagwell et al. | |
| 2013/0018305 A1 | 1/2013 | Bagwell et al. | |
| 2013/0018331 A1 | 1/2013 | Bagwell et al. | |
| 2013/0158338 A1 * | 6/2013 | Kelly | A61M 25/0026 600/16 |
| 2013/0237930 A1 | 9/2013 | Mulvihill et al. | |

FOREIGN PATENT DOCUMENTS

| | | | | |
|---|---|---|---|---|
| DE | 102010026774 A1 * | 1/2012 | | A61B 1/122 |
| JP | H08275918 A | 10/1996 | | |
| JP | 09-098749 | 4/1997 | | |
| JP | 2002523131 A | 7/2002 | | |
| JP | 2013529480 A | 7/2013 | | |
| WO | 94/03226 A1 | 2/1994 | | |
| WO | WO-9403226 A1 * | 2/1994 | | A61M 16/04 |
| WO | 2004098654 A2 | 11/2004 | | |
| WO | 20041108051 A2 | 12/2004 | | |
| WO | 2005/067647 A2 | 7/2005 | | |
| WO | 2006/071855 A2 | 7/2006 | | |
| WO | 2006/074283 A2 | 7/2006 | | |
| WO | 2007/090057 A2 | 8/2007 | | |
| WO | 2007/098376 A2 | 8/2007 | | |
| WO | 2008/059647 A1 | 5/2008 | | |
| WO | 2011158244 A2 | 12/2011 | | |

OTHER PUBLICATIONS

Supplementary Partial European Search Report issued in corresponding European Patent Application No. 15749385 dated Oct. 10, 2017, 12 pages.

Office action issued in corresponding U.S. Appl. No. 14/599,929 dated Dec. 27, 2017, 13 pages.

Office action (with translation) issued in corresponding Japanese Patent Application No. 2016-569579 dated Nov. 22, 2018, 12 pages.

English translation of Office action issued in corresponding Japanese Patent Application No. 2019-167501 dated Dec. 1, 2020, 6 pages.

* cited by examiner

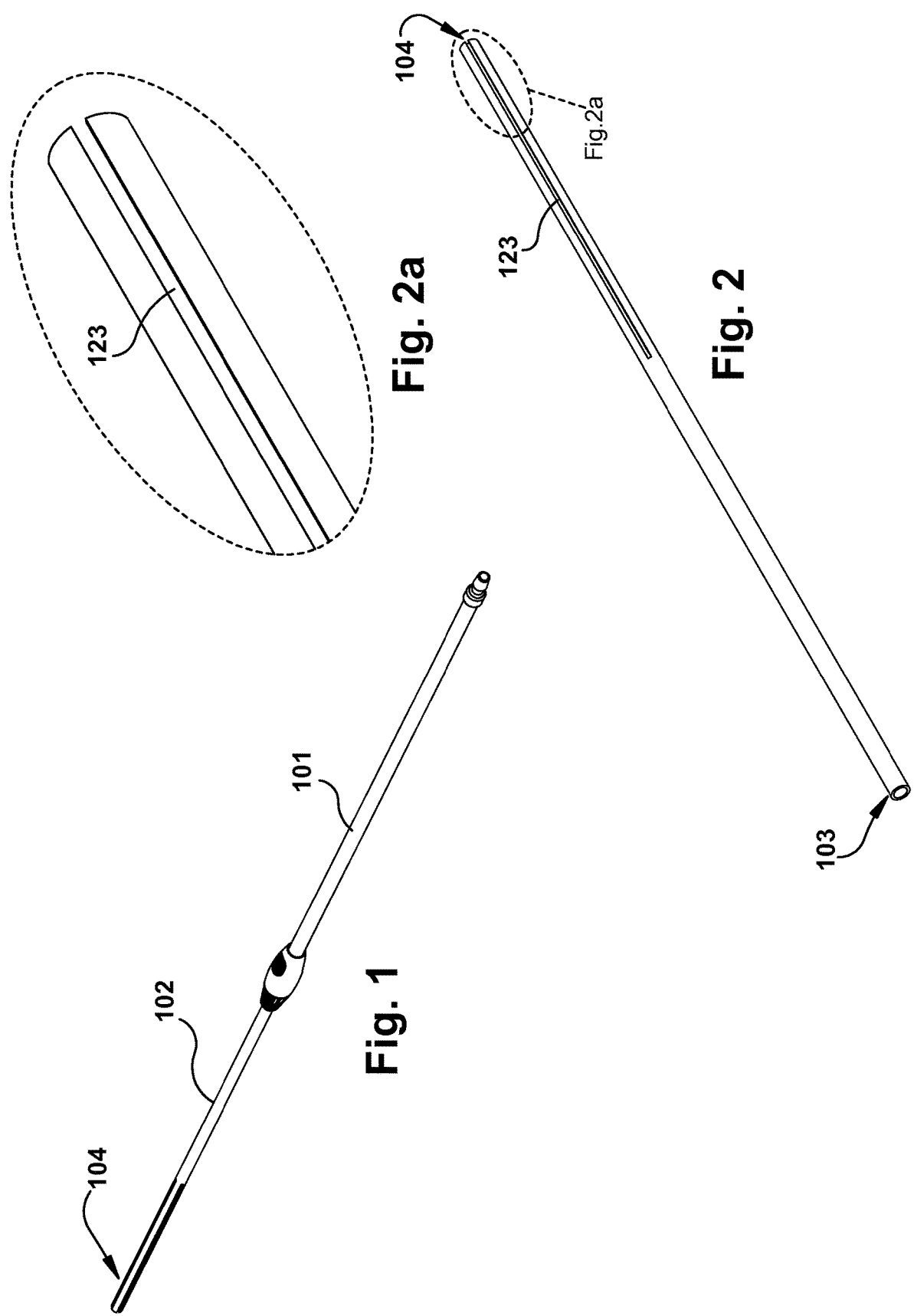

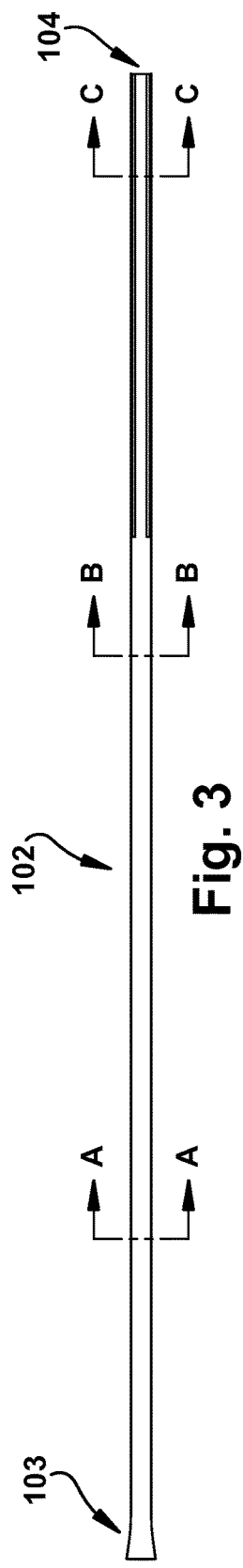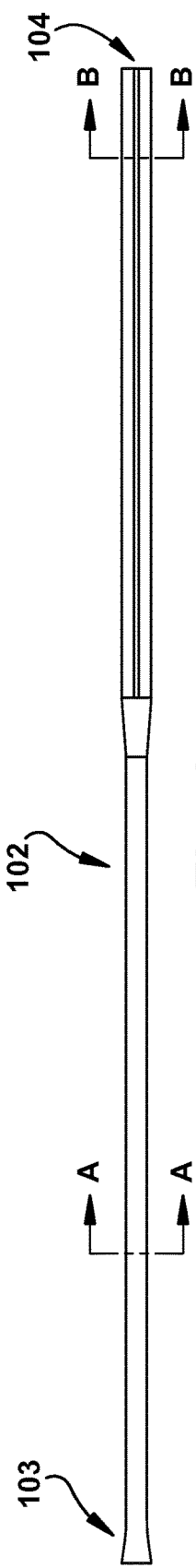

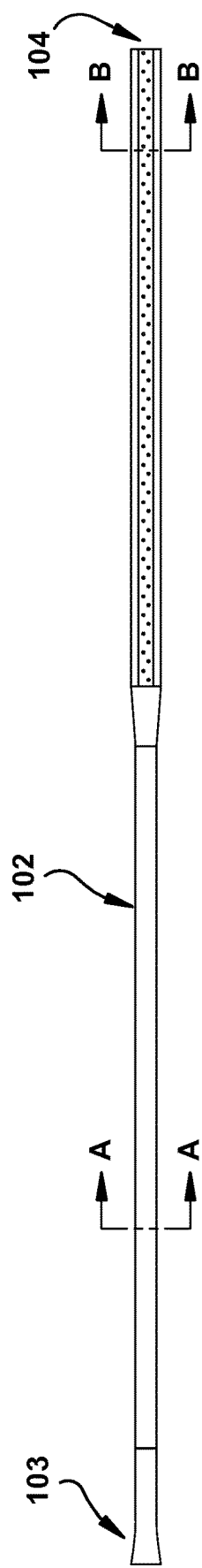

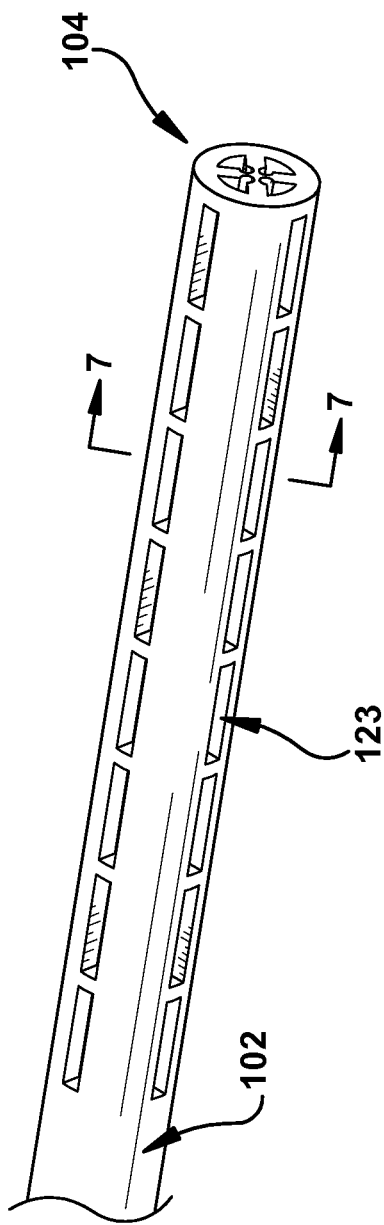
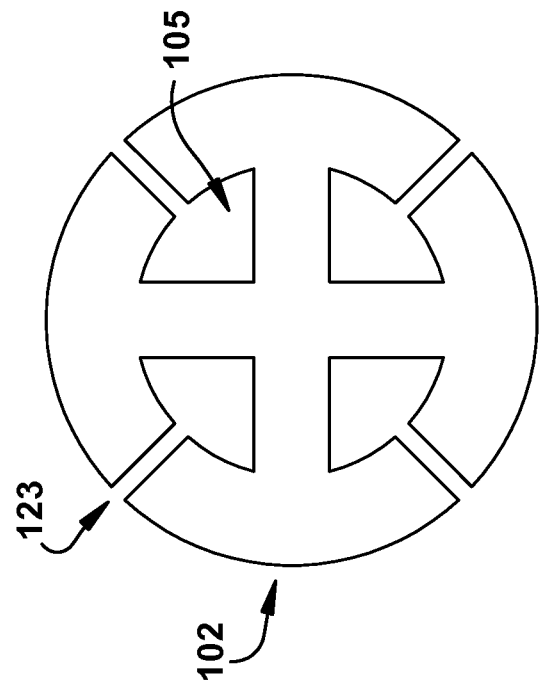
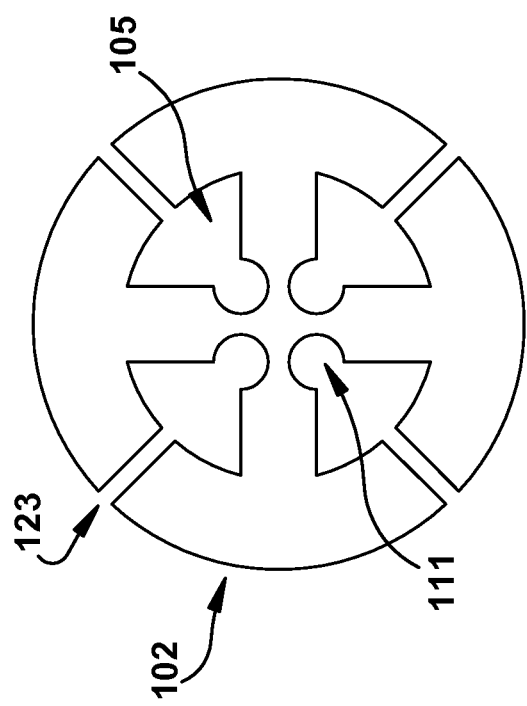
Fig. 6
Fig. 7
Fig. 8

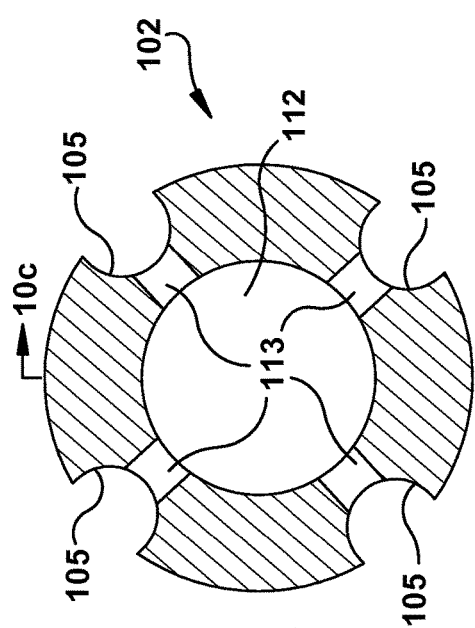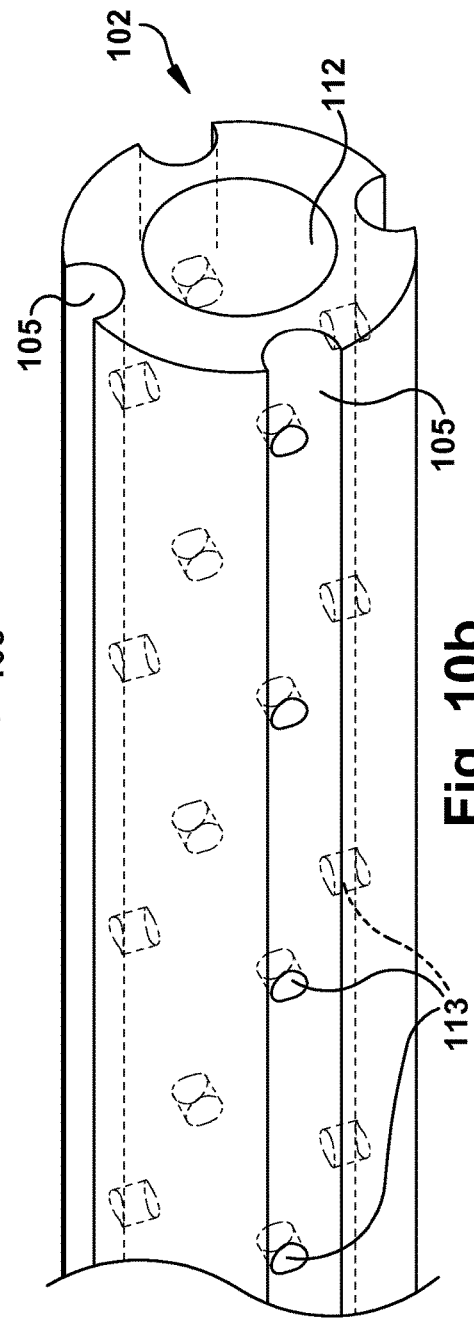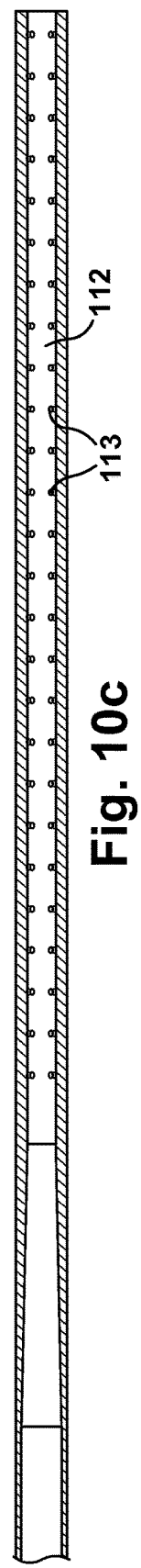

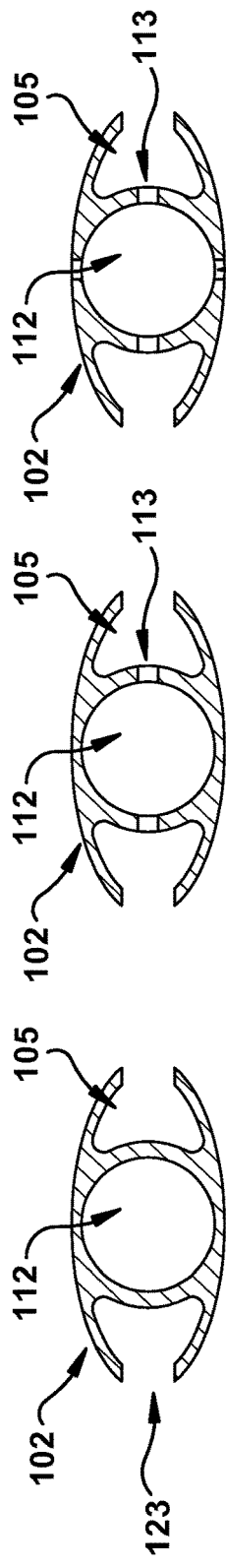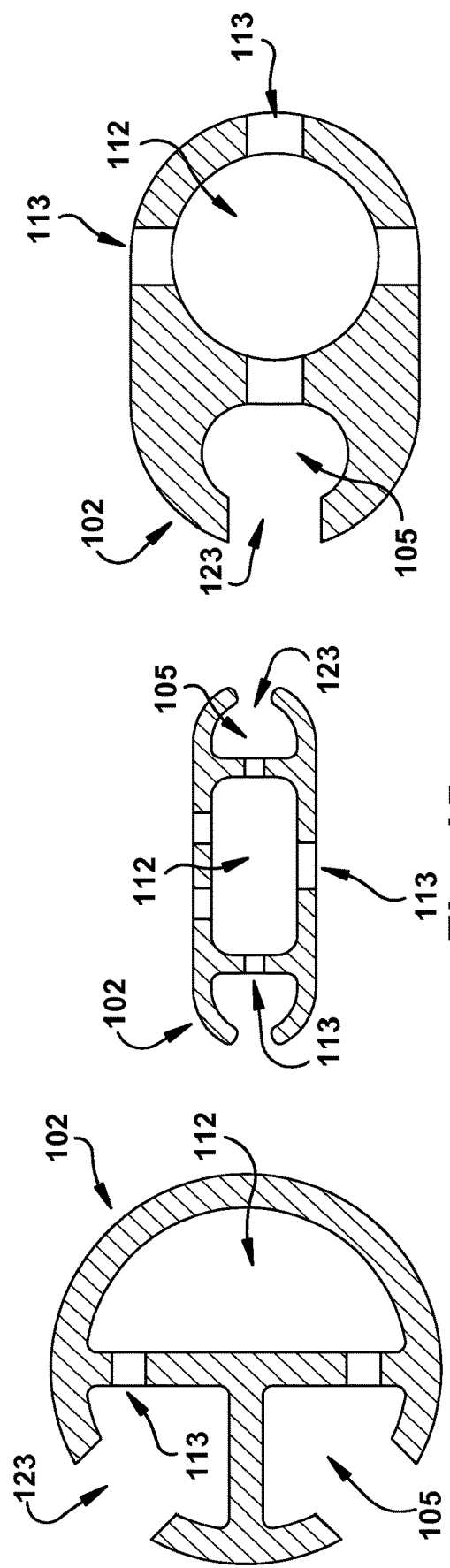

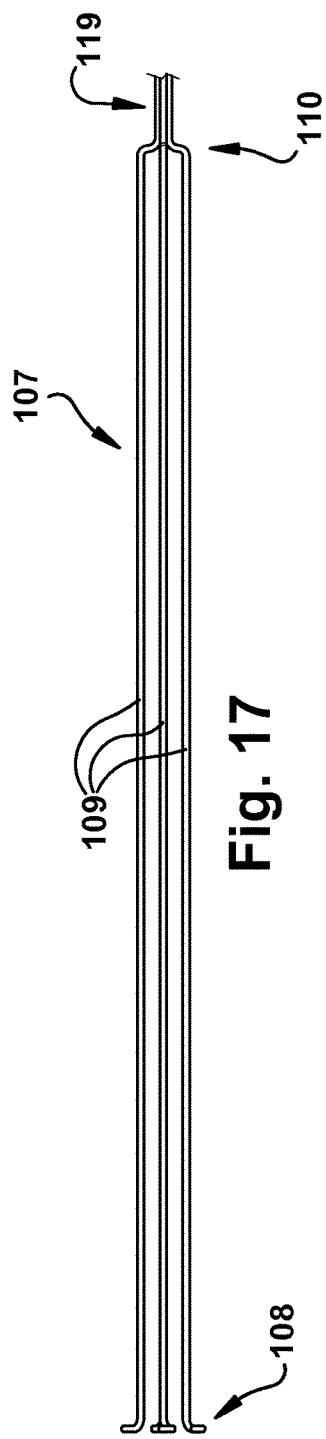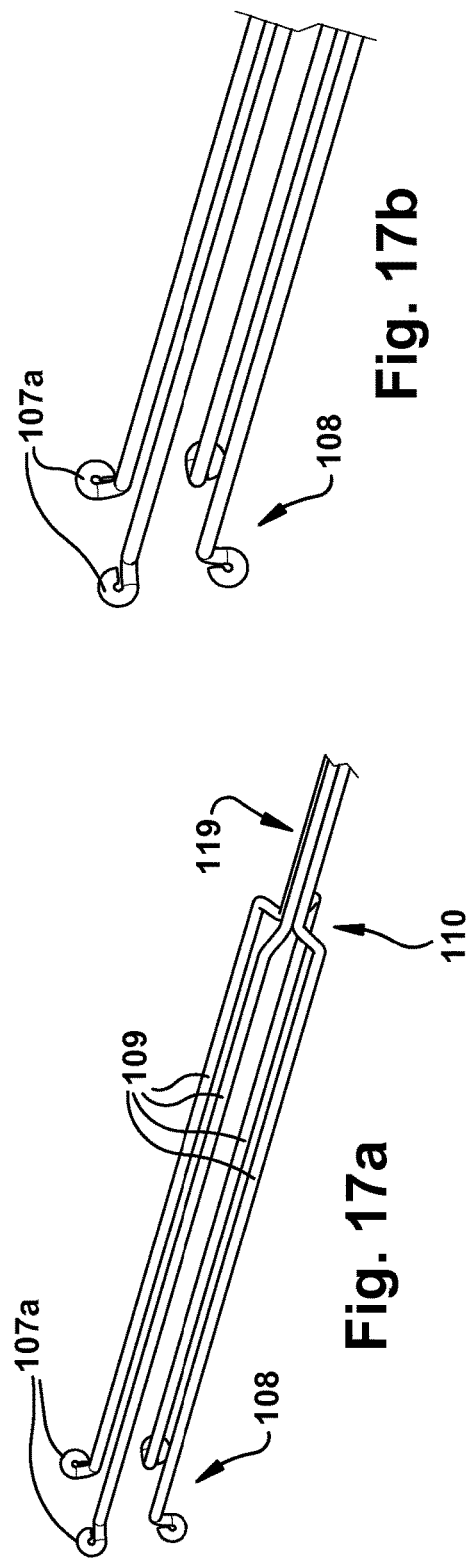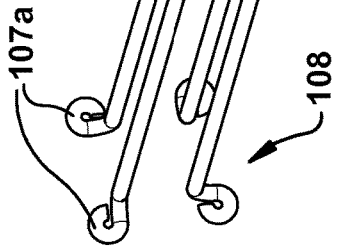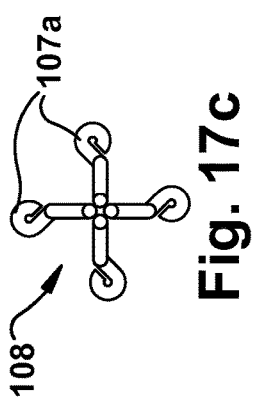
Fig. 17
Fig. 17a
Fig. 17b
Fig. 17c

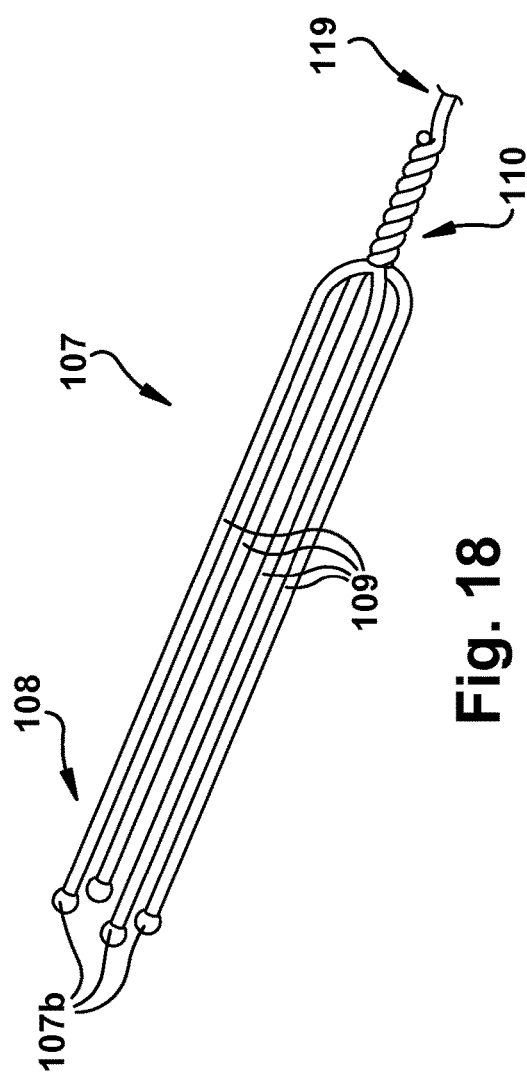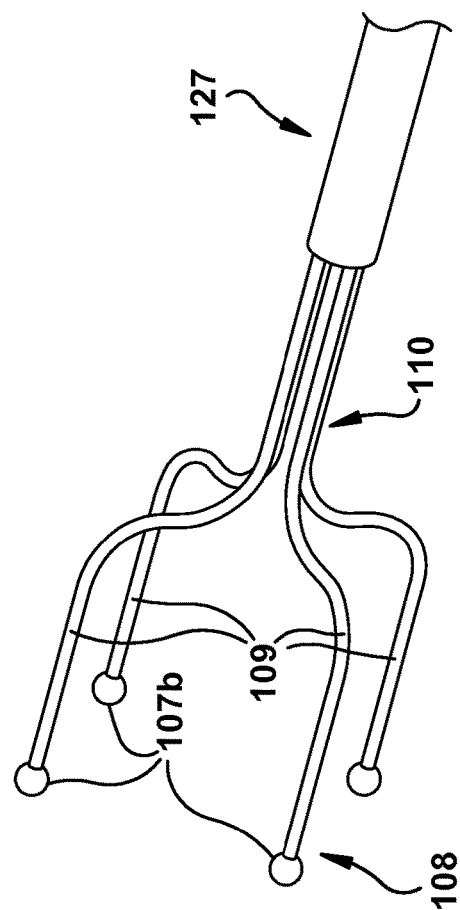

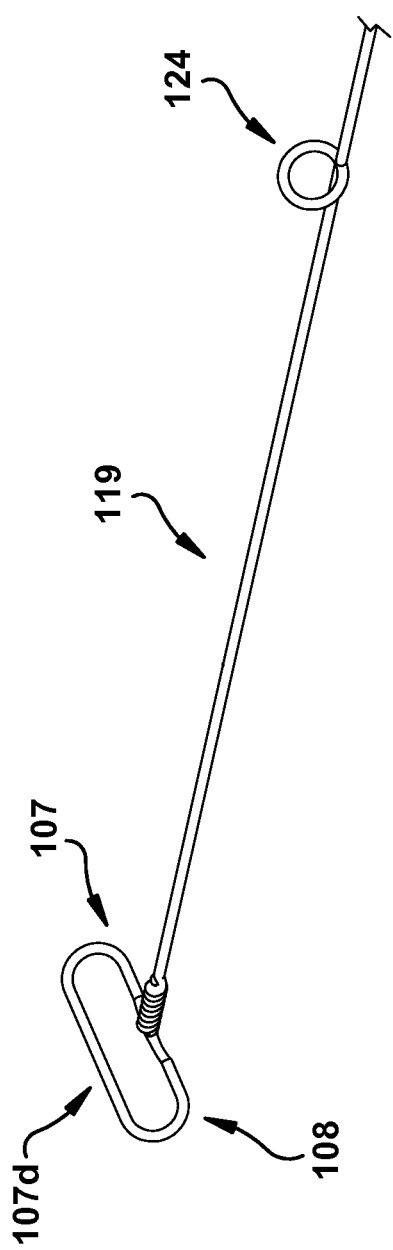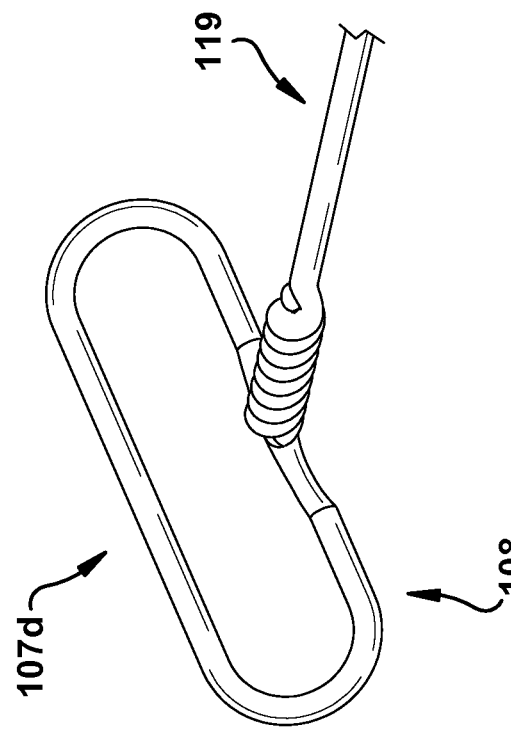
Fig. 24
Fig. 25

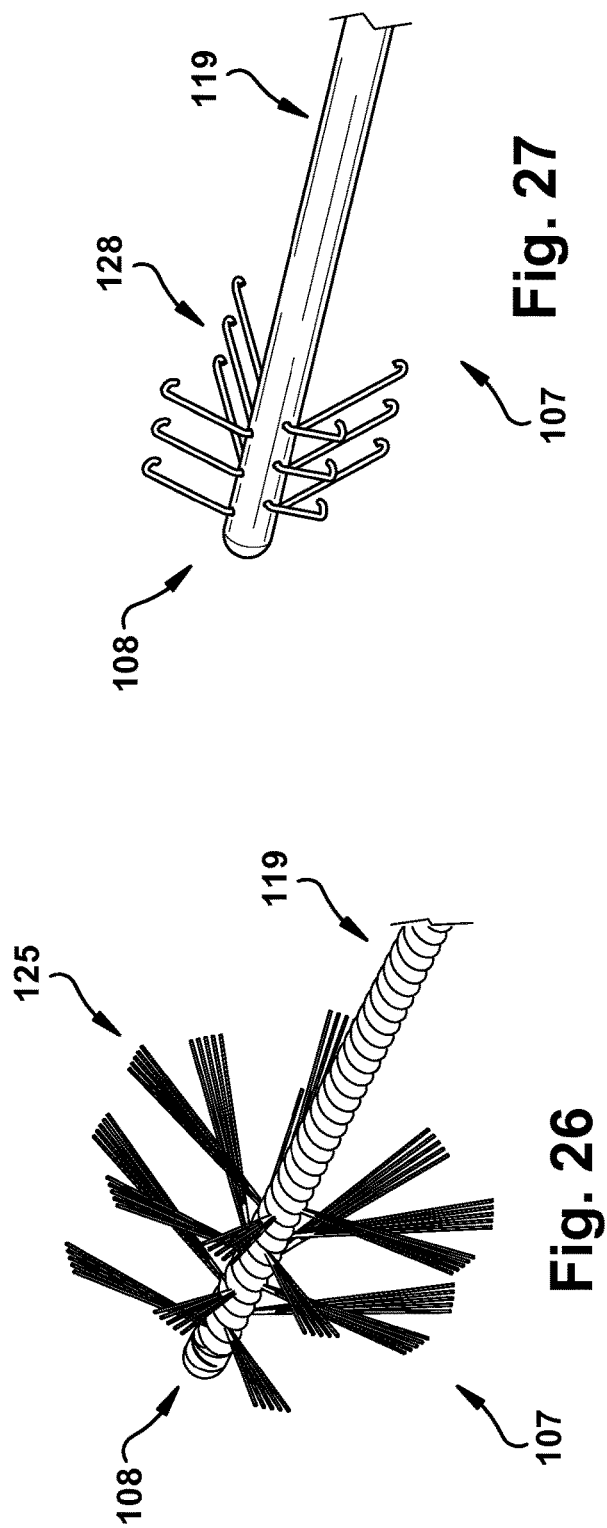

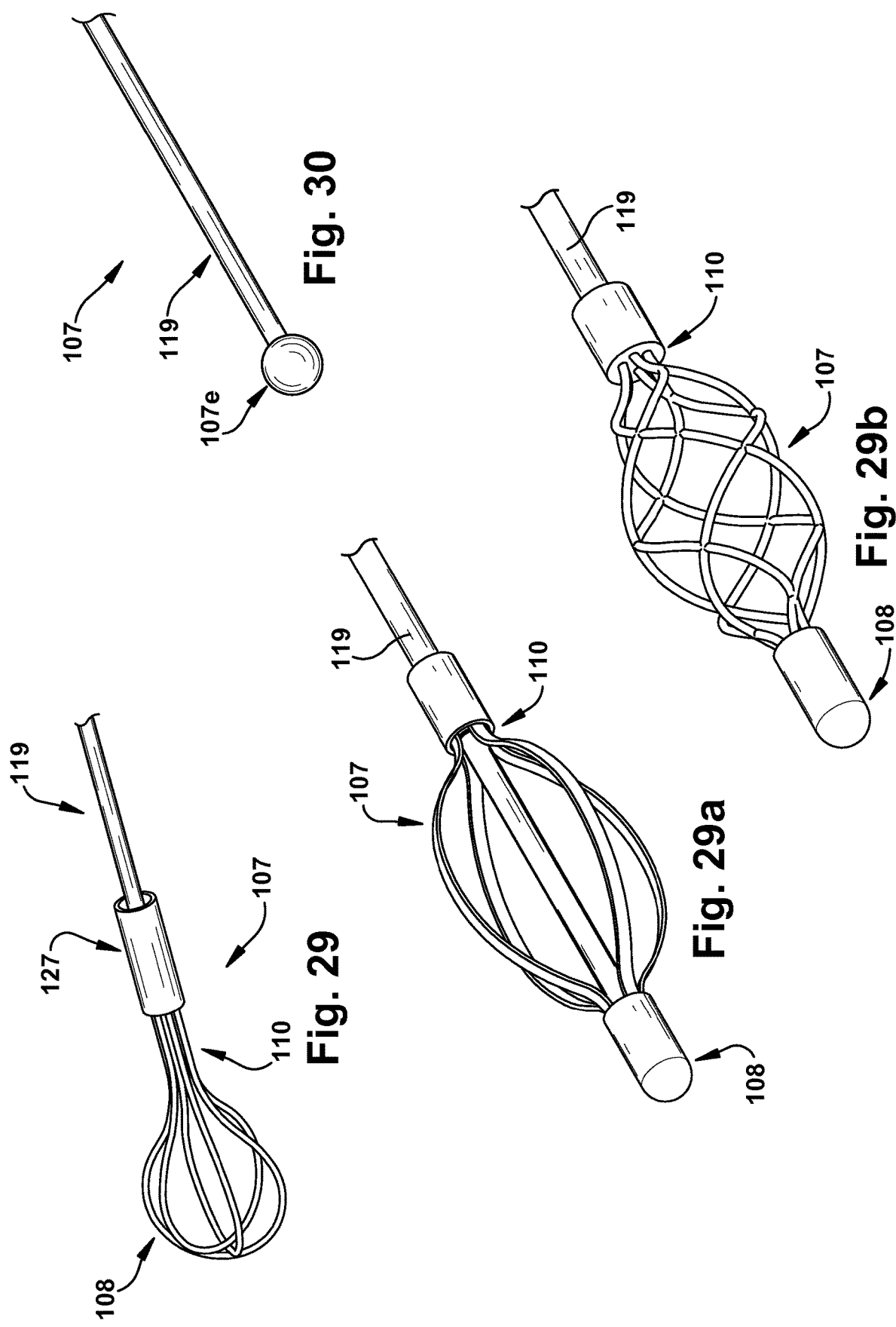

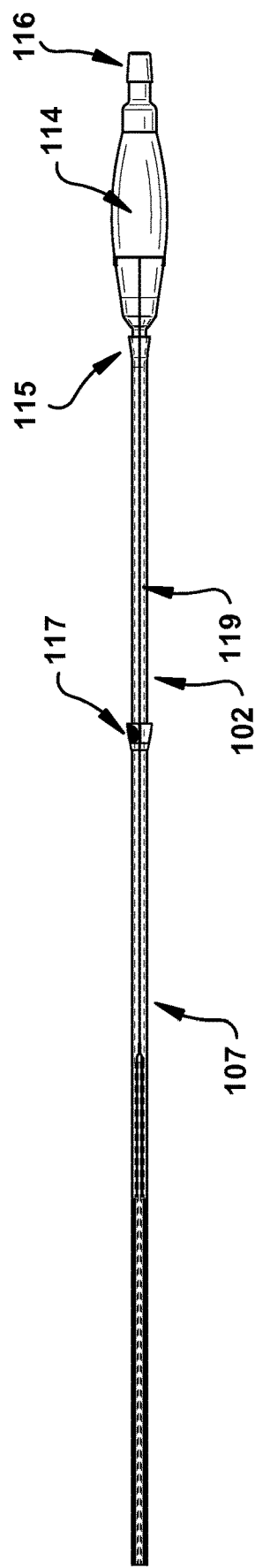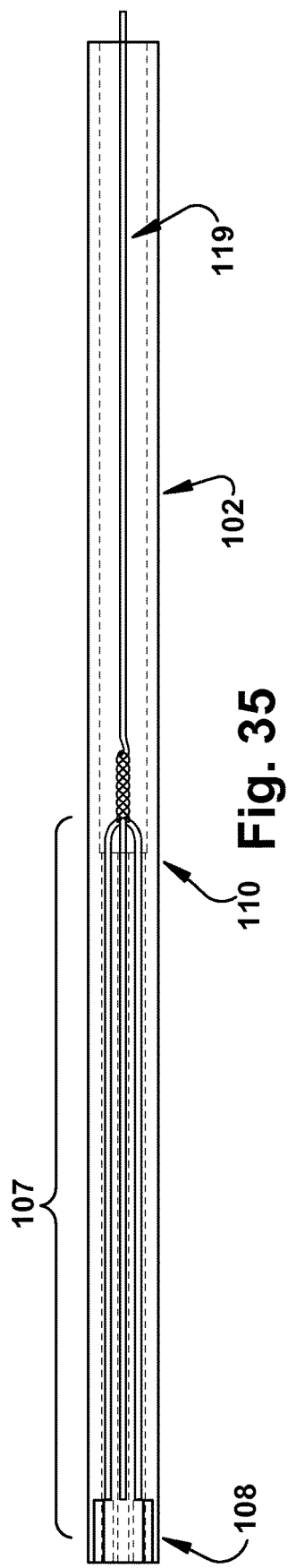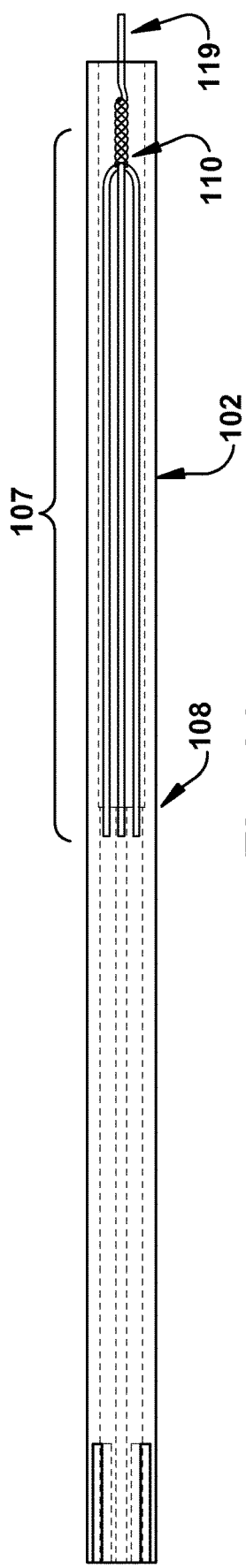

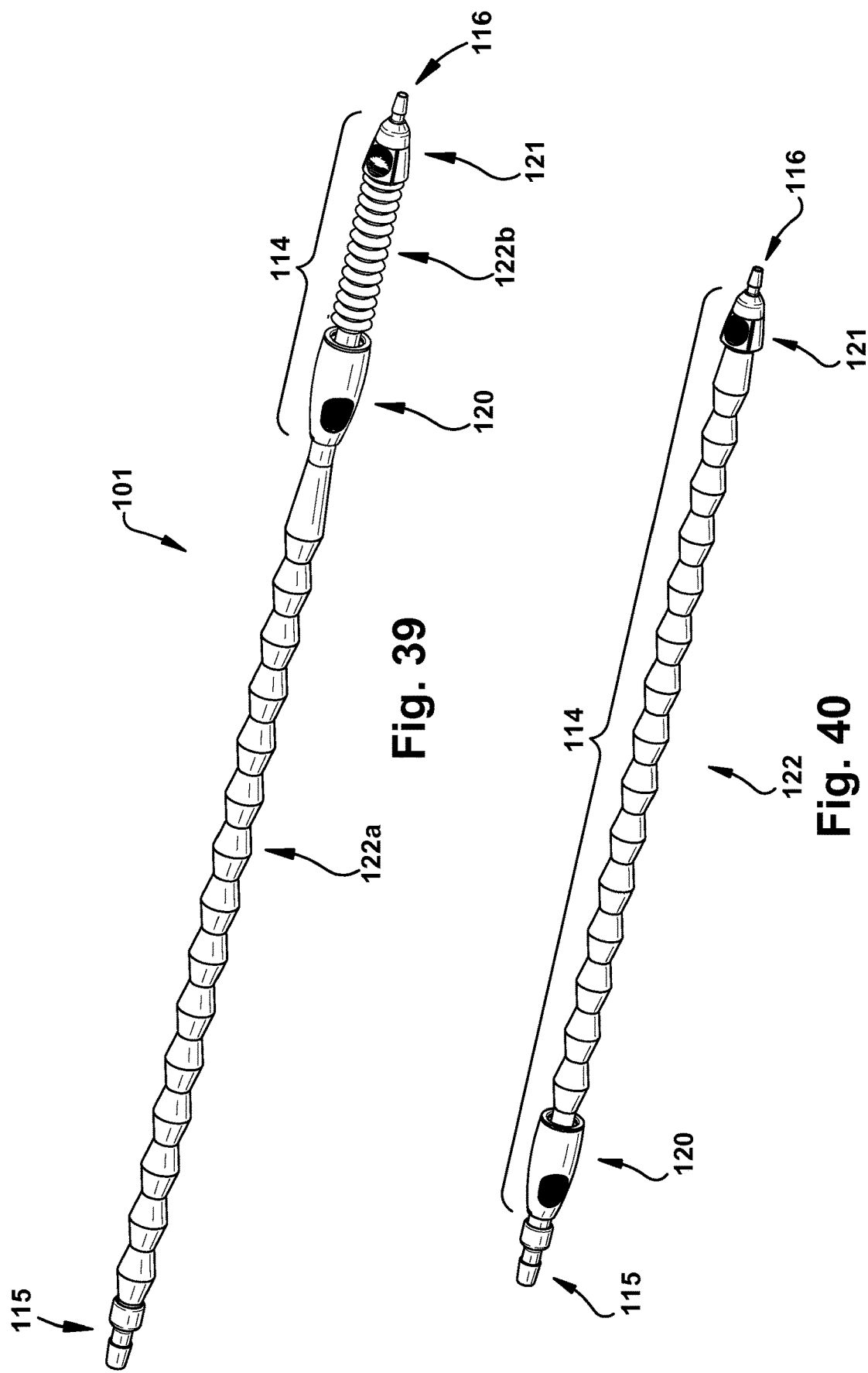

US 10,974,023 B2

MEDICAL TUBE CLEARANCE

CROSS-REFERENCE TO RELATED APPLICATIONS

This application claims the benefit of U.S. provisional patent application Ser. No. 61/940,725 filed Feb. 17, 2014, the content of which is incorporated herein by reference.

BACKGROUND

Field of the Invention

The invention relates to methods and devices to clear obstructive debris from medical tubes. More particularly, it relates to such a device having a clearance member that is formed to match a cross-section of a medical tube or to clear debris from multiple lumens in a medical tube.

Description of Related Art

Millions of medical tubes are used every year to drain bodily fluids and secretions from within body compartments and structures. For example, such tubes can be used to drain fluid from one's bladder, from the colon or other portions of the alimentary tract, or from the lungs or other organs in conjunction with various therapies. Medical tubes also are used to drain blood and other fluids that typically accumulate within the body cavity following traumatic surgery. In all these cases, a tube is inserted into the patient so that its terminal end is provided in or adjacent the space where it is desired to remove accumulated or pooled fluid and the proximal end remains outside the patient's body, where it is typically connected to a suction source.

One of the biggest categories of patients requiring medical tube drainage is patients who have had heart and lung surgery, nearly all of whom require at least one chest tube to drain the space around the heart and lungs after surgery. Chest tubes are long, usually semi-stiff, plastic tubes that are inserted into the chest in the vicinity of the heart and lungs to drain collections of fluids or air from within the pleura, the mediastinum or pericardial space, or from within the thoracic cavity generally.

Fluid and other material accumulating in the vicinity of the medical tube's distal end (within the patient) is drawn through that tube and out of the space where it accumulated via suction applied at the tube's proximal end. Ideally, the medical tube will remain free from clots and other debris that may partially or totally obstruct the suction pathway within the medical tube. Unfortunately, however, bodily secretions (particularly those including blood or blood platelets) often form clots within medical tubes, which can partially or totally obstruct the suction pathway within the tube.

Obstruction of a medical tube can impact its effectiveness to remove the fluid and other material for which it was originally placed, eventually rendering the medical tube partially or totally non-functional. In some cases, a non-functional tube can have serious or potentially life-threatening consequences. For example, if there is a blockage in a chest tube following cardiac or pulmonary surgery, the resulting accumulation of fluid around the heart and lungs without adequate drainage can cause serious adverse events such as pericardial tamponade and pneumothorax. In addition to chest tubes used in heart, lung, and trauma surgery, other medical tubes are prone to clogging as well, including feeding tubes, surgical wound drains, urinary catheters, cardiovascular catheters, and others.

There are few effective techniques to manage medical tube clogging when it occurs. During the perioperative period following chest surgery or trauma, clinicians will undertake measures to try to remove any debris (such as a clot) that has accumulated or formed within the chest tube, to keep the tube clear. One method is to simply tap the tube to try and break up the debris. Another method is referred to as "milking the tube." "Milking" involves using one's fingers, or a rudimentary device composed of a pair of pliers with rollers fashioned onto its jaws, to compress the tube over the debris to try and break it up. The goal is to loosen the debris, or to break it into smaller pieces, so it can be more readily drawn out of the tube via suction applied at the proximal end.

Another technique is fan folding. In this technique, the clinician bends the chest tube in various ways to try to break up any long clots or other obstructions that extend along the axis of the medical tube. The aim is to produce several smaller pieces of debris, as opposed to one long piece, that will be more readily drawn proximally via the suction applied at the tube's proximal end. Still another technique is known as "stripping." Here, the clinician takes two fingers lubricated in some fashion, or the improvised device composed of a pair of pliers with rollers mentioned above, and "strips" the tube. This is achieved by compressing the tube initially near where it enters the patient, and drawing the compressing apparatus (one's fingers or other compression device) proximally, with compression still applied, along the tube's length toward the suction source. This is done repeatedly to try and work any obstructive debris out from the tube and toward the suction source.

None of the above techniques is particularly effective. Moreover, they are time consuming and can be quite painful if the patient is awake and alert when they are performed, due to tugging on the medical tube. Tugging on chest tubes whose terminal ends have been placed near the pleura or pericardium can be especially painful. In addition, the "stripping" technique is known to generate short bursts of extreme negative pressure within chest tubes, which in turn draws a strong suction in the body cavity where its terminal end has been placed. This can be quite dangerous in certain circumstances. For example, negative pressures of magnitude greater than −300 cm of water can be generated adjacent suture lines on coronary anastomosis, etc., which can disrupt some of the work that was done during a prior surgery. As a result, many surgeons have banned stripping their patients' chest tubes due to the potential for complications.

When the above techniques fail to clear a potentially dangerous clot within the tube, a more invasive technique must be used. This requires establishment of a sterile field around the chest tube, which is disconnected from the suction source to manually insert a suction catheter to clear the debris. This is known as open chest tube suctioning, and it can be effective to clear a clogged chest tube. But it is highly undesirable for a number of reasons. First, it compromises the sterile field within the chest tube system by exposing the internal environment within that system to the external environment, potentially introducing bacteria inside the chest. Second, the closed system (suction source to chest tube to body space within the chest) typically must be breached to insert the catheter inside the chest tube. Breaking the seal on this system causes loss of the normal physiologic negative pressure inside the chest. This can result in lung collapse (pneumothorax) while suctioning the chest tube. Additionally, the suction catheter can easily be passed beyond the end of the chest tube, which has the potential to injure the heart or lungs, which could be life threatening. Finally, this procedure is time consuming and usually can only be performed by physicians due to the associated dangers. Thus it is only occasionally done in extreme situations when a clogged chest tube is causing a serious acute problem.

Medical tubes may vary in cross-section along their lengths. For example, a medical tube may include a single lumen near its proximal end and be partitioned into a plurality of lumens or channels at or toward the distal end. Additionally, a medical tube may have one or more openings and/or apertures that extend through the medical tube's outer wall to allow fluid to be drawn into the medical tube from its side. One example tube is partitioned at is distal end, where a plurality of openings at the distal end of the medical tube provide communication between one or more of the partitioned lumens and the space outside the medical tube inside the patient. To assist the suction typically applied to the medical tube by a vacuum source, such partitioned medical tubes may help drain fluid from the patient through capillary action via said openings. Partitioned medical tubes present a challenge for clearing obstructions from within the partitioned portion of the medical tube because a clearance apparatus may not be able to sufficiently clear each lumen of the medical tube or its partitioned portion. When a clearance apparatus is inserted into the medical tube from its proximal end, the clearance apparatus may not be able to navigate into each separate lumen, which can result in a clot or occluding material remaining in one or more of the lumens, thus decreasing the drainage capacity of the medical tube.

Currently, surgeons often implant two or more medical tubes, or employ large-diameter tubes, following surgery to provide additional drainage capacity and avoid potentially life-threatening complications of a clogged tube. Methods and apparatus are desirable to keep medical tubes (partitioned or non-partitioned) from clogging or to clear them reliably without having to breach the closed system between the suction source and the body cavity requiring drainage. Such methods/apparatus may allow surgeons to place fewer tubes post-surgery, or to select tubes having smaller diameters, both of which will reduce patient discomfort and recovery time. Placement of fewer tubes also will minimize the risk of infection.

SUMMARY

A device for clearing obstructions from a medical tube is provided. The device includes an elongate guide member and a clearance member attached to or formed integrally with the guide member. The clearance member is a branched clearance member having a plurality of individual branches each configured to be received within a respective lumen within the medical tube.

A further device for clearing obstructions from a partitioned region of a medical tube is provided. The device includes an elongate guide member and a clearance member attached to or formed integrally with the guide member, wherein the clearance member is formed to substantially match a cross-sectional perimeter shape of a lumen or lumens in the partitioned region of the medical tube.

An apparatus for clearing obstructions from a medical tube is also provided. The apparatus includes a medical tube coupled to a handle assembly and an elongate guide member extending at least partially within the medical tube, wherein at least a portion of the medical tube is composed of a flexible material adapted to stretch as the handle assembly is drawn proximally away from a fixed point along a length of the medical tube.

A further device for clearing obstructions from a medical tube is also provided. The device includes an adjustable-length guide tube connected in fluid communication with a medical tube and cooperating therewith to at least partially define a pathway through which obstructions can be evacuated from the medical tube. An elongate guide member extends through the adjustable-length guide tube and the medical tube. Extension of the adjustable-length guide tube results in withdrawal of the guide member relative to the medical tube, and collapse (i.e. contraction) of the adjustable-length guide tube results in advancement of the guide member relative to the medical tube.

A method of clearing obstructions from individual distinct lumens in a partitioned region of a medical tube is also provided. The method includes the following steps: translating an elongate guide member that is at least partially disposed within the medical tube, thereby correspondingly translating a clearance member attached to or formed with the guide member through the medical tube, wherein the clearance member includes a plurality of branches, each said branch being received and translating within a respective one of the distinct lumens.

An assembly is also provided, which includes a medical tube. The medical tube has a proximal region and a distal region. A primary lumen extends through the medical tube in both said proximal and distal regions thereof. At least one secondary lumen extends in the distal region of the medical tube and is separated from the primary lumen by an interior wall of the medical tube. The secondary lumen is configured as a channel substantially open to a space outside the medical tube. The primary and secondary lumens are in fluid communication via at least one opening in the intermediate wall.

BRIEF DESCRIPTION OF THE DRAWINGS

FIG. 1 is a perspective view of a clearance apparatus coupled to a medical tube.

FIG. 2 is a perspective view of a medical tube with openings (slits in the illustrated embodiment) in the sidewall of the tube extending along a portion of the length of the tube.

FIG. 2a is a close-up perspective view of a distal end of the medical tube of FIG. 2.

FIGS. 3-5 illustrate medical tubes having variable cross-sections along their respective lengths.

FIG. 3 is a side view of an exemplary partitioned medical tube as described herein.

FIG. 3a is a cross-sectional view of the medical tube of FIG. 3 taken along line A-A therein.

FIG. 3b is a cross-sectional view of the medical tube of FIG. 3 taken along line B-B therein.

FIG. 3c is a cross-sectional view of the medical tube of FIG. 3 taken along line C-C therein.

FIG. 4 is a side view of another exemplary partitioned medical tube as described herein.

FIG. 4a is a cross-sectional view of the medical tube of FIG. 4 taken along line A-A therein.

FIG. 4b is a cross-sectional view of the medical tube of FIG. 4 taken along line B-B therein.

FIG. 5 is a side view of another exemplary partitioned medical tube as described herein.

FIG. 5a is a cross-sectional view of the medical tube of FIG. 5 taken along line A-A therein.

FIG. 5b is a cross-sectional view of the medical tube of FIG. 5 taken along line B-B therein. The distal region (corresponding to the cross-section in this figure) includes perforations through the side wall of the medical tube as seen in FIG. 5.

FIG. 6 is a perspective view of a partitioned distal region of a medical tube with apertures in the sidewall thereof along a portion of its length.

FIG. 7 is a cross-sectional view of the partitioned region of the medical tube shown in FIG. 6 taken along line 7-7 therein.

FIG. 8 is a cross-sectional view of an alternative embodiment of the medical tube shown in FIG. 6.

FIG. 10a is a cross-sectional view of a distal partitioned region of a medical tube according to yet another embodiment as described herein, wherein secondary lumens are in the form of channel U-shaped channels that are fully open to lateral space exterior to the medical tube.

FIG. 10b shows a perspective view of the partitioned region of the medical tube shown in FIG. 10a.

FIG. 10c shows a longitudinal cross-section of the medical tube shown in FIG. 10a, wherein the primary lumen undergoes a convergence in a transitional region between an unpartitioned region (to the left in the figure) and the partitioned region shown in FIG. 10a.

FIG. 11 is a cross-sectional view of a partitioned medical tube or region thereof according to another embodiment as described herein.

FIG. 12 is a cross-sectional view of a partitioned medical tube or region thereof according to still another embodiment as described herein.

FIG. 13 is a cross-sectional view of a partitioned medical tube or region thereof according to still another embodiment as described herein.

FIG. 14 is a cross-sectional view of a partitioned medical tube or region thereof according to still another embodiment as described herein.

FIG. 15 is a cross-sectional view of a partitioned medical tube or region thereof according to still another embodiment as described herein.

FIG. 16 is a cross-sectional view of a partitioned medical tube or region thereof according to still another embodiment as described herein.

FIG. 17 is a side view of a clearance member according to an embodiment hereafter described.

FIG. 17a is a rear perspective view of the clearance member of FIG. 17.

FIG. 17b is a close up rear perspective view of the distal end of the clearance member of FIG. 17.

FIG. 17c is a front view taken from the distal end of the clearance member of FIG. 17.

FIG. 18 is a rear perspective view of a clearance member according to another embodiment hereafter described.

FIG. 19 is a rear perspective view of a clearance member according to yet another embodiment hereafter described.

FIG. 24 is a rear perspective view of a clearance member according to yet another embodiment hereafter described.

FIG. 25 is a close up rear perspective view of a distal end of the clearance member of FIG. 24.

FIG. 26 is a close up rear perspective view of a clearance member according to yet another embodiment hereafter described.

FIG. 27 is a close up rear perspective view of a clearance member according to yet another embodiment hereafter described.

FIG. 28 is a close up rear perspective view of a clearance member according to yet another embodiment hereafter described.

FIG. 29 is a close up rear perspective view of a clearance member according to yet another embodiment hereafter described.

FIG. 29a is a close up front perspective view of a clearance member according to yet another embodiment hereafter described.

FIG. 29b is a close up front perspective view of a clearance member according to yet another embodiment hereafter described.

FIG. 30 is a perspective view of a clearance member according to still another embodiment hereafter described.

FIG. 34 is a side view of a clearance apparatus coupled to a medical tube having a partitioned distal region, showing a guide member and a clearance member advanced within the medical tube, according to an embodiment hereafter described.

FIG. 35 is a close-up side view of the distal region of the medical tube illustrated in FIG. 34, showing a clearance member of the clearance apparatus having respective branches corresponding to individual lumens of the partitioned distal region of the medical tube fully inserted therein.

FIG. 36 is a close-up side view as in FIG. 35, but with the clearance member (branches) partially withdrawn.

FIG. 39 is a perspective view of a clearance apparatus according to an embodiment hereafter described.

FIG. 40 is a perspective view of a clearance apparatus according to another embodiment hereafter described, which has no separate proximal guide tube. The guide tube shown is in an expanded configuration.

DETAILED DESCRIPTION OF PREFERRED EMBODIMENTS

Figure 10:
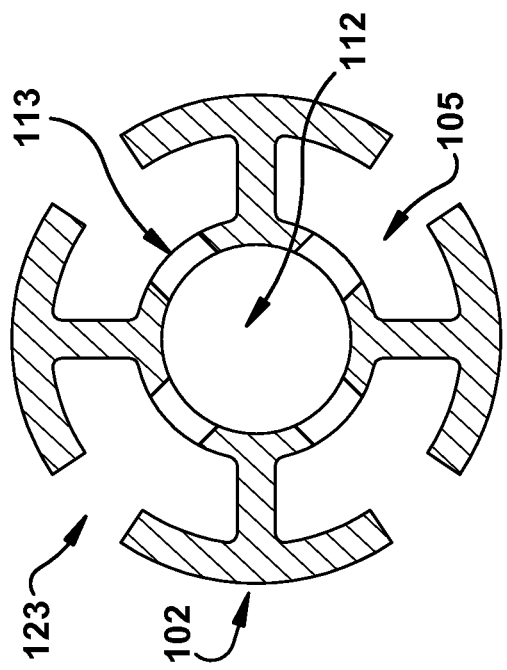
FIG. 10 is a cross-sectional view of a partitioned medical tube or region thereof according to another embodiment as described herein.

As used herein, the terms proximal and distal are generally to be construed with reference to a patient that has been or is to be fitted with a medical tube, such as a chest tube. For example, the distal end or region of a medical tube (e.g. chest tube) is that end or region that is to be inserted into or disposed more adjacent (e.g. within) the patient during use, as compared to the opposite end or region of the medical tube (e.g. chest tube). Similarly, a distal element (or the distal side or region of an element) is nearer to the patient, or to the distal end of the chest tube, than a proximal element (or the proximal side or region of an element). Also herein, the "terminal" end of a tube, wire, or member refers to its distal end.

FIG. 1 shows a representation of a clearance apparatus 101 coupled to an exemplary medical tube 102 that is partitioned near its distal end 104. The medical tube 102 has at least one lumen and one or more openings 123 in fluid communication with one or more lumens within the tube 102. In the embodiment of FIG. 1, the medical tube includes only one lumen. The lumen extends from or near the distal end 104 to the proximal end 103. The openings 123 extend from at or near the distal end 104 along a portion of the length of the medical tube 102. In use fluid can be drawn into the lumen by capillary action or a pressure gradient (e.g. via a connected vacuum/suction source, vacuum pump, compressed bulb, or other means). FIGS. 2 and 2a more clearly illustrate the medical tube 102 with openings 123 along a portion of the length of the medical tube near its distal end 104. The medical tube 102 can be attached at its proximal end 103 to a clearance apparatus 101. Preferably, the medical tube 102 is made from a material having elastic properties, such as silicone, which will help ensure a fluid-tight seal. A flexible, elastic medical tube 102, e.g. made from silicone, also will result in reduced discomfort for the patient compared to more rigid medical-tube materials, such as polypropylene or polyethylene. However, if desired these and other rigid materials may be used. Other materials, including various thermoplastics and thermosets, also may be used in place of silicone, if desired. Preferably, the medical tube 102 is made from a clear (i.e. transparent or substantially transparent) plastic material, so the operator of the clearance apparatus 101 described herein can visualize any clot material or other debris therein, as well as its removal as described below. Aspects and embodiments of the medical tube 102 hereafter described can be applied directly or with minor and routine modifications to clear obstructive debris from a variety of medical tubes used in different applications, for example chest tubes, catheters, surgical drain tubes to drain fluid from other structures or orifices, endotracheal tubes, feeding tubes, gastric tubes, or tubes to deliver material to or from the alimentary tract, etc.

Exemplary embodiments of partitioned medical tubes will now be more fully described. As seen in FIGS. 3-5, medical tubes 102 can be provided that vary in cross-section along their lengths. In one embodiment illustrated in FIGS. 3-3c, a medical tube 102 having a generally round or circular perimeter (circumference) can include a plurality of regions having different cross-sections, each region having a respective number and arrangement of lumens or channels therein. The embodiment illustrated in FIGS. 3-3c includes three distinct regions: a proximal region whose cross-section is shown at FIG. 3a, an intermediate region whose cross-section is shown at FIG. 3b, and a distal region whose cross-section is shown at FIG. 3c.

The proximal region constitutes a single lumen such that this region is configured as a conventional tube. As shown in FIG. 3a, the medical tube 102 in this region is substantially hollow having a single lumen of open cylindrical cross-section. As shown in FIG. 3b the intermediate region is divided into four substantially equivalent wedge-shaped lumens arranged symmetrically as shown. As shown in FIG. 3c, in the distal region slits or apertures are disposed along the length of the tube 102 through its outer wall so that the wedge-shaped lumens in the intermediate region give way to correspondingly arranged and similarly-shaped channels that are open laterally to the space surrounding the tube 102 adjacent the exterior surface thereof, through the aforementioned slits or apertures. It is to be noted that as used herein, the term 'lumen' includes both enclosed passages, which are not open laterally to the outside of the medical tube, as well as channels, which are passages that are open to the outside via slits, apertures or other openings that provide fluid communication through the wall of the medical tube. A lumen also can be open to an adjacent lumen within the medical tube via slits, apertures or other openings, whether or not it is also open to the outside through the wall of the medical tube.

In another embodiment illustrated in FIGS. 4-4b, the medical tube 102 can be round in shape along a portion of its length near its proximal end 103 and transition into a flattened shape along a portion of its length near its distal end 104. This type of medical tube can be referred to as a flat channel drain. As shown in FIG. 4a taken along line A-A in FIG. 4, a first region of the medical tube 102 in this embodiment has a single lumen of open cylindrical cross-section similar to a conventional tube. But as one proceeds along its length toward the distal end, the medical tube 102 in this embodiment transitions from that of the first region described above adjacent the proximal end 103 to a second region adjacent the distal end 104, which has a flattened, oblong-shaped cross-section featuring two flat longer sides and two rounded shorter sides. FIG. 4b, taken along line B-B in FIG. 4, shows a cross-section of the medical tube 102 in this second region wherein the tube is partitioned into four distinct channels, two of which are substantially rectangular in cross-section and disposed opposite one another adjacent the opposed flat sides of the tube, and two of which are substantially semicircular in cross-section and disposed opposite one another adjacent the opposed curved sides. In the illustrated embodiment each of the channels is open to the environment immediately surrounding the tube via respective slits or apertures that provide fluid communication through the tube wall.

Yet another embodiment is illustrated in FIG. 5, which also shows a flat channel drain embodiment of a medical tube 102. The first, proximal region in this embodiment whose cross-section is shown in FIG. 5a taken along line A-A in FIG. 5, is similar to the preceding embodiment; i.e. it is a single lumen having a cylindrical cross-section as in a conventional tube. However, unlike the preceding embodiment the second region here, whose cross-section is shown at FIG. 5b taken along line B-B in FIG. 5, has a single closed lumen whose cross-section is oblong and substantially ovoid in shape, having flat sides and curved sides that are parallel to the respective flat and curved outer walls of the tube in this region. A plurality of longitudinally-extending ribs are disposed along the length of one flat side of the oblong lumen in the second region of the medical tube 102 in this embodiment, defining intermediate channels therebetween. These ribs may impart a degree of flexural strength to the medical tube 102 in the second, flat-channel region. They may also aid in maintaining a channel or channels for fluid flow in the instance where the tube becomes kinked or crushed.

FIGS. 6-7 illustrate partitioned medical tube 102 according to a further embodiment. Specifically, FIG. 6 shows the distal end of a medical tube 102, which is partitioned into four substantially equivalent quadrant lumens 105 arranged symmetrically as shown, each having an arcuate outer wall radially distant from the longitudinal axis of the tube 102, and a longitudinally-extending slot 111 opposite the arcuate wall adjacent the axis. As better seen in FIG. 7, which shows a cross-section taken along line 7-7 in FIG. 6, the quadrant lumens 105 are separated and defined by substantially orthogonally, longitudinally-extending radial cross-members that substantially form a cross or plus sign (+) when viewed end-on. In this embodiment the slots 111 communicating with each of the respective lumens 105 are substantially circular in cross-section. As will be described below, in preferred embodiments the slots 111 can accommodate respective guide members (e.g. guide wires) for actuating, as by translation, associated clearance members within the respective lumens 105.

FIG. 8 illustrates a cross-section similar to that in FIG. 7 except without the aforementioned slots 111, which may be undesirable or unuseful in case no guide member/wire is to be accommodated therein for clearing the respective lumens 105. In a further alternative (not shown), fewer than all (for example only one) of the lumens 105 may have associated slots 111.

Figure 9:
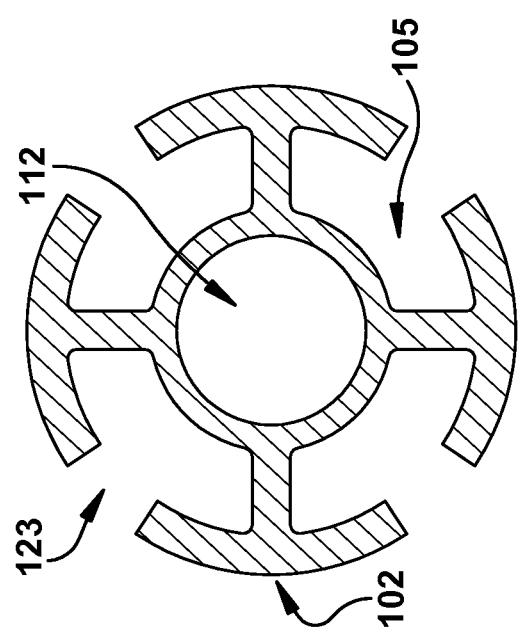
FIG. 9 is a cross-sectional view of a partitioned medical tube or region thereof according to another embodiment as described herein.

In another embodiment illustrated in FIG. 9, a medical tube 102 or portion thereof can include a cross-section with a primary lumen 112 disposed at the center and coaxial with the central axis of the tube 102, and a plurality of secondary lumens 105 (which can be channels open laterally to the outside as illustrated) positioned about the outer circumference of the primary lumen 112. In FIG. 9, four secondary lumens 105 are arranged circumferentially and aligned 90° apart forming essentially arcuate channels spaced apart adjacent the outer circumference of the primary lumen 112. In FIG. 9 (as well as in FIGS. 6-8) openings 123 penetrate through the side wall of the medical tube 102 and extend along a length of the tube 102 at least in the vicinity of the pictured cross-section; e.g. from at or near the distal end 104. The openings 123 provide fluid communication between each secondary lumen 105 and the external environment adjacent the opening. The embodiment illustrated in FIG. 10 is similar to that of FIG. 9, with the addition of openings 113 through the wall defining the primary lumen 112 to provide fluid communication between the primary lumen 112 and each of the secondary lumens 105.

FIGS. 10a-10c illustrate a further embodiment of a medical tube 102 having a partitioned region at the distal end of the tube. In this embodiment the secondary lumens 105 are configured as U-shaped channels that are fully open to the space laterally adjacent and outside the medical tube. In the partitioned region, each of the secondary lumens 105 is in fluid communication with a centrally-disposed primary lumen 112 via pluralities of respective openings 113 spaced longitudinally in the walls separating the primary lumen 112 from each respective lumen. The partitioned region is located remote from the proximal end of the medical tube 102. Beginning from a location proximal to the partitioned region, preferably from the proximal end of the medical tube, the primary lumen 112 has a cross section greater than that of the primary lumen 112 in the partitioned region; preferably in this location the primary lumen 112 is the only lumen in the tube and consequently can have a maximal cross section suitable for efficient drainage. As the primary lumen 112 extends distally from the aforementioned location it reaches a transition region where its cross section converges from the aforementioned maximal cross section to a reduced cross section. The convergence of the primary lumen makes room for secondary lumens 105 to be positioned in the tube 102 in the partitioned region, for example spaced laterally about and extending parallel to the primary lumen 112. In this embodiment, the partitioned region is disposed distally in the medical tube, preferably adjacent the distal end, and configured to be implanted within the body cavity or orifice of the patient requiring drainage. The secondary lumens 105 serve to aid fluid drainage into the primary lumen 112, which may be connected in-line with a vacuum source to draw collected fluids and other debris from the body cavity/orifice. Because only the primary lumen 112 is fully enclosed about its perimeter it is the primary location where obstructions are most likely to form. Accordingly, active clearance of only the primary lumen 112 should be effective to maintain tube patency. This embodiment avoids multiple relatively small-diameter lumens, e.g. as in the intermediate region of the medical tube in FIG. 3, where much of the tube clogging would typically occur.

In this embodiment the longitudinally-variable primary lumen 112 may be cleared by any appropriately sized clearance member. More optimal clearance may be achieved using a clearance member 107 that can adjust to the cross section of the primary lumen 112 as it transitions from the medical tube 102 proximal end 103 to distal end 114. Clearance members 107 shown in FIGS. 20 and 26-29b can be manufactured from spring steel or shape memory alloy such as Nitinol so that lateral compressive forces act on the clearance member 107 as it advances through a region where the lumen transitions from larger to smaller cross-section, thereby deforming the clearance member so that it conforms to an overall smaller cross-section complementary to that of the smaller-diameter region of the lumen 112. The clearance members of FIGS. 26-27 utilize branches or wires that extend laterally and are cantilevered from the guide member 109 or otherwise from a central portion of the clearance member. The clearance members of FIG. 28 is a spiral-wound member, such as a wire, which can be made of elastic shape-memory material having a resting conformation slightly larger than the largest cross-section or diameter to which it must conform in the lumen 112 in use. The clearance members of FIGS. 29-29b are wire-form clearance members, formed of one or a plurality of shaped wires that are bent or formed so that together they form an overall three-dimensional structure; for example a bulb or whisk in FIG. 29, an oblong spheroid in FIG. 29a and an ellipsoid in FIG. 29b. These wire-form clearance members also are preferably formed from a shape-memory, elastic material such that in their resting condition they conform to an overall cross-section or diameter slightly larger than the largest cross-section or diameter to which they must conform in use. In each case, the elasticity of the clearance member allows it to conform to different cross-sections or diameters of the primary lumen 112, or at least to adjust to the available cross-section within the lumen at a given location, to facilitate clearance of different regions. For example, the clearance member according to any of the above-described embodiments can conform to the smaller cross-sectional region of a lumen 112 (e.g. at or adjacent a distal end of a medical tube 102), and upon withdrawal through the tube 102 into a larger cross-sectional region of the primary lumen 112, the elastic and/or shape memory properties of the clearance member will tend to return it to approximately its original shape, such that it will assume a conformation having a larger overall cross-section conforming to the larger-diameter region of the lumen 112. By 'conform' it is not meant that the cross-section of the clearance member necessarily matches or is complementary to that of the lumen 112 (though this is one possible embodiment, particularly when the lumen has a circular cross-section). Rather, 'conform' simply means that the cross-section of the clearance member expands to adapt to the available cross-sectional area within the lumen at a given location.

In addition to its ability to conform to a variable cross-section primary lumen 112, clearance members formed of elastic material as above described also can conform to kinks and constrictions that may be imparted to the medical tube 102, and to the primary lumen 112 therein, as a result of bending to conform to or navigate body structures and organs within the body of a patient. This feature may prove useful for clearing a medical tube 102 that follows a tortuous path.

In an alternative embodiment to that illustrated in FIGS. 10a-10c, the primary lumen 112 may have an internal cross-section that stays consistent from the proximal end of the medical tube to the distal end of the medical tube. It can be appreciated that in this configuration the wall thickness in the proximal region that does not have secondary lumens will become thicker. Alternatively the overall diameter/cross-section of the medical tube in the proximal region will be smaller than in the region having secondary lumens.

FIG. 11 shows an additional embodiment, wherein the cross-section of a medical tube or region thereof has three lumens: a primary lumen 112 having a semi-circular cross-section, constituting substantially one-half of the total cross-sectional area of the tube in this region, and two quadrant or secondary lumens 105 in the form of channels open to the outside constituting the opposite half of the overall tube cross-section. Openings 123 are positioned along a portion of the exterior wall of the medical tube 102 adjacent each secondary lumen 105 to provide fluid communication between each such lumen 105 and the external environment. Perforations or openings 113 in the wall separating the primary lumen 112 from each of the secondary lumens 105 provide fluid communication between each of the secondary lumens 105 and the primary lumen 112.

FIGS. 12-16 illustrate further embodiments of medical tubes 102 configured substantially as flat-channel drains. For example, FIGS. 12-14 show similar embodiments wherein the tube 102 has a substantially ellipsoid cross-section with a central primary lumen 112 having a substantially circular cross-section concentric with the longitudinal axis of the tube 102. A pair of secondary lumens 105, each having a substantially trapezoidal-shaped cross-section with curved walls and being the mirror image of the other, are arranged on opposite sides of the primary lumen 112. In each of the illustrated embodiments of FIGS. 12-14, openings 123 in the side wall of the tube 102 provide fluid communication between each of the secondary lumens 105 and the exterior environment adjacent the medical tube 102, such that the secondary lumens 105 are configured as channels. In the embodiments of FIGS. 13 and 14, openings 113 (e.g. slots or perforations) are provided in the walls separating the primary lumen 112 from the secondary lumens 105 to provide fluid communication between them. Pluralities of such openings can be spaced periodically and longitudinally along the medical tube 102. Alternatively, the openings 113 an be configured as slots that extend a partial or appreciable length of the medical tube, preferably at or adjacent its distal end. The embodiment shown in FIG. 14 includes additional openings 113 in the side wall of the medical tube between the primary lumen 112 and the external environment, thus providing fluid communication therebetween. Again, these openings can be configured and disposed similarly as described above.

The embodiment of the medical tube 102 shown in FIG. 15 has a substantially rectangular cross-section. A substantially rectangular-shaped primary lumen 112 is centrally positioned in the tube 102 with a pair of substantially semi-circular shaped disposed on opposite sides of the primary lumen 112 adjacent the short sides of the medical tube when viewed in cross-section. Each semi-circular shaped lumen 105 can be provided with fluid communication with the exterior environment outside the tube via openings 123 in the side wall of the tube, for example in the vicinity of its distal end that would be inserted within a patient cavity during use, in order to drain fluids present in that vicinity. Also as before, internal openings 113 can be provided in the walls separating the primary lumen 112 and each secondary lumen 105. Still further, additional openings 113 can be provided in the long-side walls of the tube 102 to provide communication between the primary lumen 112 and the external environment. Such openings 113 and 123 can be disposed and configured in the tube of this embodiment similarly as already described.

Each of the aforementioned medical tubes has possessed a symmetric cross-section such that the left side is a mirror image of the right side when viewed in cross-section. However, asymmetric tubes (when viewed in cross-section) are also within the scope of this disclosure. In one alternative embodiment shown in FIG. 16, an ovoid-shaped medical tube 102 can include, e.g., a circular-shaped primary lumen 112 offset from the center of the medical tube so that its axis is not the same as the central axis of the medical tube. A substantially oval-shaped secondary lumen 105 is positioned adjacent the opposite rounded side-wall of the medical tube 102 in the illustrated embodiment, wherein an opening 123 in the side wall of the tube 102 provides fluid communication between the external environment and the lumen 105. Additionally, openings 113 in the outer walls of the tube 102 adjacent the primary lumen 112, as well as in the interior wall separating the two lumens, provide fluid communication between the secondary lumen 105, the primary lumen 112 and the external environment. Again, these openings 113 and 123 can be disposed and configured as already described.

Regardless of the relative positioning and orientation of the plurality of distinct lumens running parallel within a medical tube or within a region of a medical tube, a multi-branched clearance member can be configured to match the lumen configuration in order to provide simultaneous clearance of the plurality of lumens. Returning for example to the multi-lumen configurations illustrated in FIGS. 7 and 8, a multi-branch clearance member, e.g. as illustrated in FIGS. 17-17c can be configured to provide respective clearance elements corresponding to and aligned with each of the respective lumens in order to provide effective and simultaneous clearance of each. The clearance member 107 (FIG. 17) can be provided, for example, at or formed as part of the distal end of an elongate guide member 119 that can be actuated from a more proximate location relative to the patient. Any suitable actuation mechanism effective to translate or otherwise actuate the clearance member 107 in or through the correspondingly and respectively arranged lumens for clearance thereof can be used. One exemplary actuation device is disclosed, for example, in U.S. Pat. No. 7,951,243, which is incorporated by reference. However, other suitable actuation mechanisms may be advantageously used.

Returning to the embodiment of FIGS. 17-17c, the clearance member 107 is disposed at and in a preferred embodiment integrally formed with or as the distal end of an elongate guide member 119, which can be reversibly advanced into and through the medical tube 102 to break up and/or withdraw obstructive debris therefrom (also described below). In one embodiment, the guide member 119 can be in the form of a guide wire, and the clearance member 107 can be formed by the guide wire, or by a plurality of wires that are intertwined to provide the guide member 119 but which are unwound and separated to provide distinct branches 109 of the clearance member 107 as hereafter described. In the illustrated embodiment, the clearance member 107 is configured for use in a medical tube 102 that is partitioned into a plurality of lumens 105 configured substantially as illustrated in the cross-sections of FIG. 7 or 8, at least at or adjacent the tube's distal end 104.

Referring now to FIG. 17, the exemplary multi-branched clearance member 107 has a plurality of wires that are bundled together at a proximal end 110 where it meets (or transitions from) the guide member 119. The individual wires can be intertwined, twisted, wound into a helix or parallel to one another. In an alternative embodiment, the wires may be bundled at their proximal end 110 by a retaining member that holds the wires together, or they may be welded together. In one of the aforementioned configurations the bundled wires may form the guide member 119 itself. The individual wires are separated into four distinct branches 109 on approach of the distal end 108 of the clearance member 107, each constituting a respective clearance element aligned and adapted to clear an associated one of the lumens in the medical tube 102. That is, the wires are separated such that the resulting branches 109 are spatially arranged to fit within the lumens of a complementarily-partitioned medical tube 102. As seen in FIGS. 17a-17c, in the illustrated embodiment the terminal end of each individual wire/branch 109 is wound to form a loop 107a. The diameter of each loop 107a can be selected, for example, to substantially correspond to the circumference of the inner wall of a corresponding lumen 105 of the medical tube 102 to which the clearance member 107 will be fitted, as described in more detail below. Other configurations besides loops are also contemplated to match the cross-sectional perimeter shape of the lumens to be cleared, as will also be described below. The length of the clearance member 107 is preferably dimensioned to correspond to a length of a partitioned region of the medical tube 102 to allow the clearance member 107 to break up and/or withdraw debris from within the partitioned portion of the medical tube 102, for example upon translation from a fully-advanced state within the aforesaid partitioned region to a substantially fully withdrawn state relative to said region.

In a further embodiment, the terminal end of each individual wire branch 109 of the clearance member 107 can include a sphere 107b as shown in FIG. 18. The diameter of each sphere 107b again is preferably selected to provide a sphere whose cross-sectional dimension substantially corresponds to that of the lumen 105 of the medical tube 102 in which it will be actuated to clear debris. The embodiment of FIG. 18 also illustrates bundling the wires of the clearance member 107 at their proximal end 110 by twisting the wires together with a single-wire guide member 119.

Similar to FIG. 18, FIG. 19 illustrates an embodiment with spheres 107b disposed or formed at the terminal ends of the branches 109 of the clearance member 107. As compared to the embodiments in FIGS. 17 and 18, the individual wires of the embodiment of FIG. 19 are arranged farther apart from each other, as would be appropriate in case of a medical tube having a corresponding and complementary multi-lumen configuration. In this embodiment the lengths of the branches 109 of the clearance member 107 are also shorter than in earlier-illustrated embodiments, which would correspond to a similarly-shorter multi-lumen region of a medical tube 102 in which the clearance member 107 is to be effective to clear debris. It will be appreciated that the number, arrangement, spacing and length of the branches 109 of a multi-branch clearance member 107 as herein described can be selected to correspond to the complementary features in the multi-lumen region of the medical tube 102 to be cleared. Additionally, FIG. 19 shows an embodiment where the wires forming the branches 109 are bundled at the proximal end 110 of the clearance member 107 by a retaining member 127 that holds the wires together.

Figure 20:
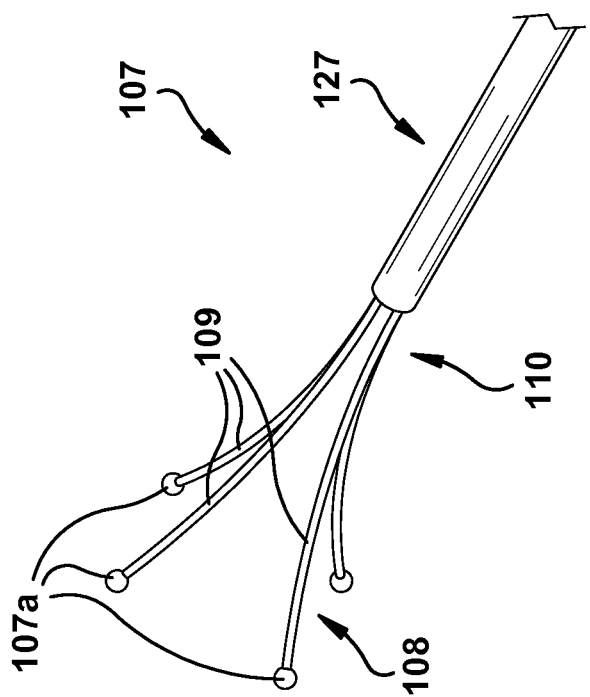
FIG. 20 is a rear perspective view of a clearance member according to yet another embodiment hereafter described.

In the embodiments of FIGS. 17-19, the wires of the clearance member 107 are arranged to correspond with particular lumens of a partitioned medical tube 102. FIG. 20 illustrates another embodiment of a clearance member 107 comprising a plurality of branches 109 that are bundled together at their proximal end 110 by a retaining member 127, but which radiate away from one another and away from a central axis of the clearance member 107. In this embodiment, the branches 107 are made of a flexible, preferably shape-memory material so that they retain a degree of rigidity and stiffness, yet can be bent to follow the contour of a particular lumen upon being forcibly advanced therein. Configured in this manner, the individual branches 107 are not arranged to correspond to complementarily arranged lumens 105. Instead, upon advancement toward and into a multi-lumen region of a medical tube 102 respective ones of the branches 107 will encounter and enter respective lumens, and upon further advancement will be forcibly conformed to follow the paths defined by those lumens. Upon continued advancement and subsequent retraction into/from those lumens, or alternatively upon other actuation such as vibration, sonication, etc., each branch 107 can effectively clear a respective lumen 105.

Figure 21:
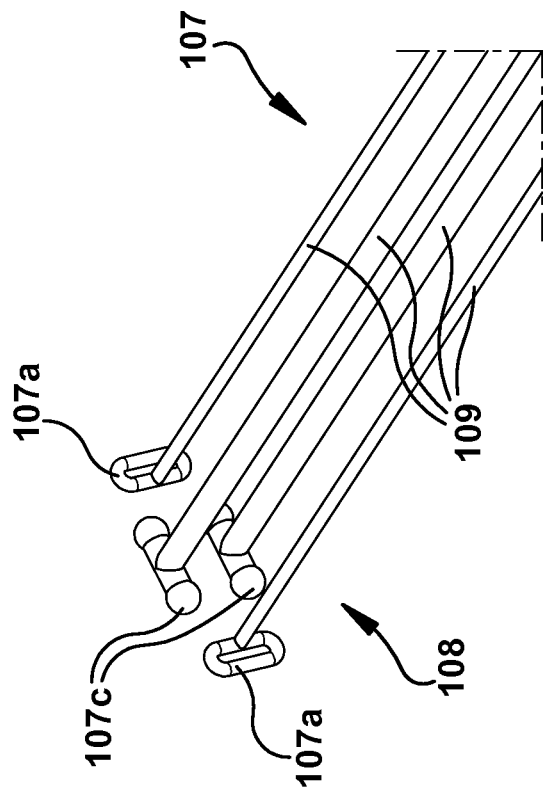
FIG. 21 is a close up rear perspective view of a distal end of a clearance member according to yet another embodiment hereafter described.

FIG. 21 shows another exemplary embodiment of a clearance member 107 for a partitioned flat-channel drain, this one configured to clear the lumens within the medical tube configuration illustrated in FIG. 15. In this embodiment, the terminal ends of the branches 109 aligned to clear the secondary channels 105 in FIG. 15 are configured as loops 107a, which can approximate the perimeters of the respective channels 105 in cross-section. Capsules 107c are at the terminal ends of the branches that are arranged to be inserted into primary lumen 112 in FIG. 15. As will now be appreciated, multiple branches 109 and their associated clearance elements at their distal ends (if present) can be configured and arranged to jointly enter and clear a common lumen. Alternatively, the clearance member 107 of this embodiment could be utilized to clear a four-lumen medical tube 102, such as for example the one illustrated in FIG. 4. In this embodiment, the branches 109 having the capsule 107c clearance elements would be aligned and utilized to enter and clear the two rectangular-shaped lumens on the longer sides of the medical tube 102 in FIG. 4, while the other two branches 109 having the loops 107a would be aligned and utilized to enter and clear the two semicircular-shaped lumens adjacent the shorter sides of the medical tube 102. The dimensions of each loop 107a and capsule 107c are preferably selected to substantially correspond to the dimensions of the inner wall of a lumen 105 of the medical tube 102 to which the clearance member 107 will be fitted. It can be appreciated that for clearance of the lumen configuration of FIG. 15 a clearance member with fewer clearance elements of appropriate shape may be used.

Figure 23:
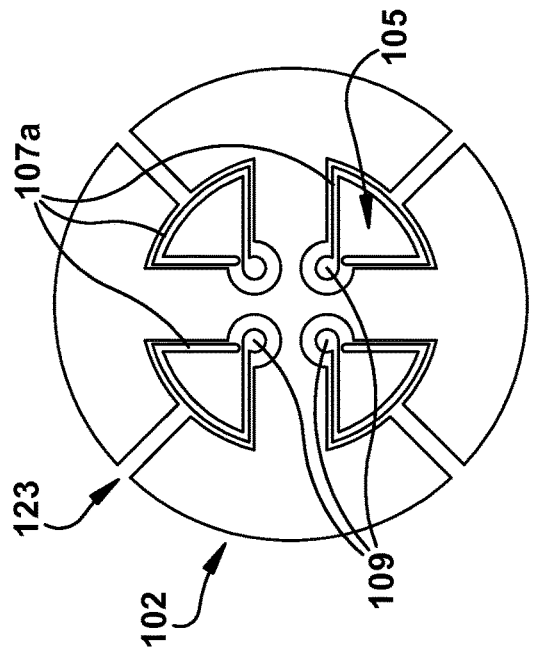
FIG. 23 is a cross-sectional view as in FIG. 7 showing a multi-branched a clearance member disposed within the respective lumens of the medical tube.
Figure 22:
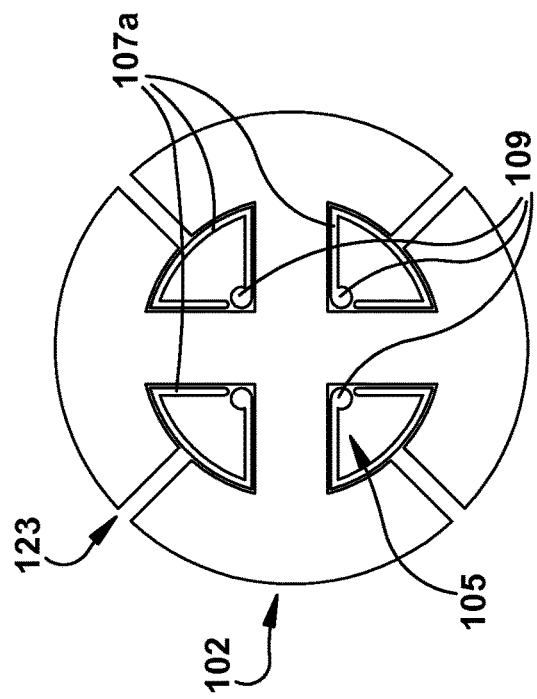
FIG. 22 is a cross-sectional view as in FIG. 8 showing a multi-branched clearance member disposed within the respective lumens of the medical tube.

FIGS. 22 and 23 show cross-sections of the partitioned medical tubes of FIGS. 8 and 7, respectively, wherein the clearance member 107 of FIG. 17 has been inserted such that its respective branches 109 extend into the correspondingly-arranged lumens 105. As discussed above, each loop 107a is preferably selected to substantially correspond to the circumference or other lateral dimension(s) of the inner wall of the associated lumen 105. Each loop 107a also provides a substantially unobstructed pathway through each lumen 105 where the loop is located regardless whether the clearance member 107 (and accordingly the loop 107a) is at rest or being actuated to clear debris within the lumen 105. Additionally, in the embodiment of FIG. 23 the guide member 119 is received within and extends through the slot 111 associated with each of the lumens 105 within the tube 102. This arrangement helps guide translation of the clearance member 107 and its associated branches 109 through the respective lumens in the multi-lumen region of the tube.

When actuating the multi-branched clearance member 107, it is preferably not retracted so far that the branches 109 thereof become entirely withdrawn from their respective lumens 105. This is because realignment and insertion of the branches 109 within the respective lumens 105 will be difficult and perhaps impossible in clinical situations where the tube 102 is inserted within a patient and visualization of the multi-lumen region within the tube may be impossible or obscured. Alternatively, even if the multi-lumen region can be visualized it could be difficult to realign all branches 109 with their associated lumens 105 for reinsertion. For example, FIGS. 35-36 (discussed in more detail below) illustrate side views of a multi-branch clearance device 107 as discussed above with respect to FIGS. 22-23 at different stages of advancement within a distal, multi-lumen region of a medical tube 102. In FIG. 35 the clearance member 107 is fully inserted so that its branches 109 penetrate to near the distal end of the individual lumens; whereas in FIG. 36 the clearance member 107 has been withdrawn so that the branches 109 are nearly but not quite fully withdrawn from the multi-lumen region. It is desired not to withdraw the multi-branched clearance member 107 to a greater extent than illustrated in FIG. 36; i.e. to such an extent that the branches 109 would be entirely withdrawn from their associated lumens in the multi-lumen region of the medical tube 102.

The embodiments illustrated in FIGS. 24 and 25 illustrate an embodiment of a clearance member 107 for use in a flat channel drain that includes regions with different cross-sections, for example, as illustrated in FIG. 5. In this embodiment, the terminal portion of the guide member 119 is wound to form an oblong-shaped loop 107d at its distal end. The loop 107d is shaped to correspond to the perimeter dimensions of the distal region of the medical tube shown in FIG. 5, and would be effective to clear debris therein. Separately, a second, circular clearance member 124 is positioned more proximally and attached along the guide member 119. The clearance member 124 is shaped to correspond to the perimeter dimension of the proximal region of the medical tube in FIG. 5, and would be effective to clear debris in that region. As will be appreciated, actuation of the guide member 119 from a proximal location will simultaneously actuate (e.g. translate, sonicate, vibrate, etc.) both the clearance members 107 and 124 in this embodiment, thus simultaneously clearing two longitudinally distinct regions of the medical tube, each having its own respective cross-section. It is to be noted that while the clearance member 107 in this embodiment is configured as a loop for a single-lumen distal region having oblong cross-section, the clearance member 107 also could be a multi-branched member as above described for clearing a multi-lumen region of the medical tube. Moreover, the loops illustrated in FIG. 24 are exemplary and correspond to the particular proximal and distal regions of the medical tube in FIG. 5. But it is to be appreciated that the loops can possess any suitable shape and may be arranged at suitable spacings to correspond to the particular medical tube to be cleared. Additionally, multiple clearance members, two or more, may be used in each longitudinally distinct region to achieve clearance along the length of the region using a given actuation.

FIGS. 26-29 illustrate additional embodiments of clearance members 107 that are configured to be insertable into a lumen of a medical tube 102, such as the primary lumen 112 shown in FIGS. 9-16. For example, the embodiment of FIG. 26 utilizes a wound spiral guide member 119. Groupings of wires or bristles 125 can extend laterally from between adjacent turnings of the guide member 119 and are preferably angled toward the proximal end of the guide member 119 to provide a wire-brush type cleaning member 107. In an alternative embodiment, rows of scraper elements 128 can be arranged around the circumference of a guide member at a distal end 108 of a clearance member 107 as shown in FIG. 27. In the illustrated embodiment, each row of scraper elements 128 includes three wires that extend laterally from the guide member 119 and form a hook at their terminal end. Each wire is angled toward the proximal end of the guide member 119. In another embodiment, a guide member 119 can be wound turning about an axis at a constant upward angle to form a helix-shaped clearance member body 109 as shown in FIG. 28. The terminal end of the wound guide member 119 can be capped with a sphere 107e to form a blunt end. In a further embodiment, FIG. 29 illustrates a clearance member 107 comprising a plurality of wire loops that are bundled and held together by a retaining member 127 to form a whisk shape at a distal end 108 of the clearance member 107. In a further alternative embodiment, the clearance member 107 as shown in FIG. 30 comprising a sphere 107e at a terminal end of a guide member 119. The sphere 107e may be sized to approximate the internal diameter of a round lumen. It may be sized substantially close to the lumen diameter, but with some clearance for the passage of fluid to prevent altering pressure within the target drainage compartment (e.g. the body orifice or cavity being drained), by a plunger effect. Alternately, it may be size larger than the diameter provided the wall of the lumen is made from an elastic material such as silicone, thereby scraping the walls of the lumen while simultaneously stretching them to loosen material. Alternatively, it may be sized substantially smaller than the lumen to allow free flow of fluid and material past the sphere. In an alternative embodiment, the distal end of the clearance member 107 can be in the form of a loop as generally discussed in U.S. Pat. No. 7,951,243, herein incorporated by reference in its entirety. A clearance member 107 configured as any one of the above, or having any alternative suitable configuration, can be provided in place of the oblong loop 107d in the embodiment shown in FIG. 24 so long as it is appropriate to clear the associated distal region of a medical tube 102.

Figure 31:
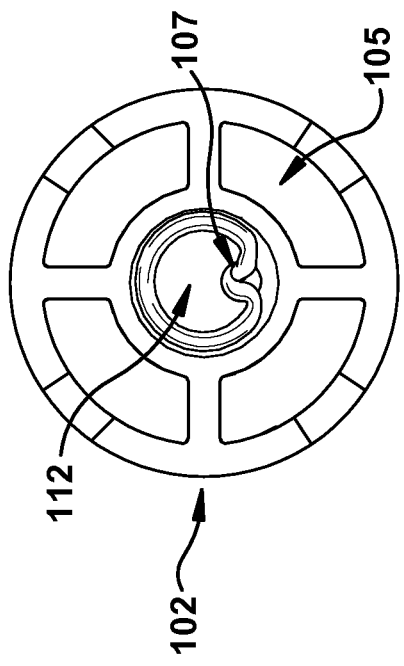
FIG. 31 is a distal-end view of the partitioned medical tube of FIG. 9 showing a loop-shaped clearance member disposed within a primary lumen of the medical tube adjacent its distal end.
Figure 33:
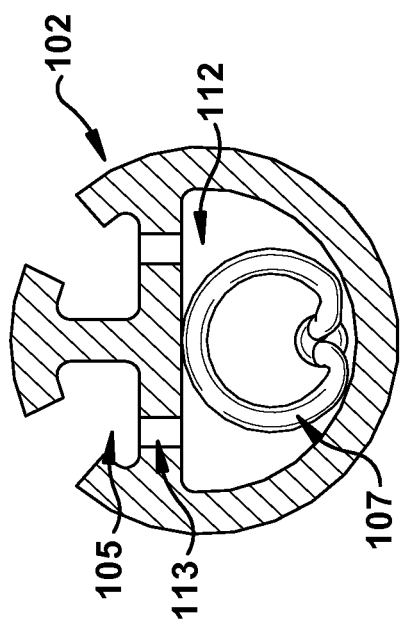
FIG. 33 is a cross-sectional view of the partitioned medical tube of FIG. 11 showing a loop-shaped clearance member disposed within a primary lumen of the medical tube.
Figure 32:
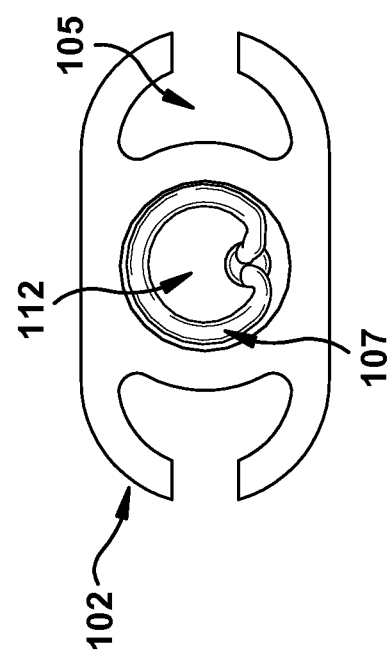
FIG. 32 is a distal-end view of a partitioned medical tube or distal region thereof according to still another embodiment showing a loop-shaped clearance member disposed within a primary lumen of the medical tube adjacent its distal end.

Alternatively or in addition, the clearance member 107 of each of the embodiments of FIGS. 26-30 can be configured to be insertable into a primary lumen 112 of a multi-lumen medical tube 102 or of a multi-lumen region of a medical tube 102, without necessarily requiring additional branches 109 to be insertable or inserted in adjacent lumens. For example, FIG. 31 shows the partitioned medical tube of FIG. 9 with a loop-shaped clearance member 107 within the primary lumen 112. The clearance member 107 is preferably selected to substantially correspond to the perimeter dimensions (in this case the circumference) of the inner wall of the lumen 112. FIGS. 32 and 33 show additional examples of partitioned medical tubes 102 with a loop-shaped clearance member 107 within the primary lumen 112. Notably, no clearance members or branches 109 are provided to clear the secondary lumens 109 in these embodiments. While the clearance member 107 embodiments illustrated in FIGS. 31-33 provide a substantially unobstructed pathway through the lumens 112, alternative clearance member embodiments may obstruct more of the pathway through the lumens 112. It can be appreciated that multiple clearance members of the same or differing configuration can be deployed along the length of the lumen.

The guide member 119 and clearance member 107 can be made from conventional materials including plastics and metals. It is preferred that the guide member 119 be made from a material having sufficient flexibility that it can reversibly bend to a radius of curvature of four centimeters, more preferably three centimeters, more preferably two centimeters or one centimeter, without snapping or substantially compromising its structural integrity. Suitable materials include, stainless steel, titanium-nickel (such as Nitinol), cobalt alloys. In addition to being sufficiently flexible to negotiate bends in the medical tube 102 on being advanced/retracted therethrough, the guide member 119 should preferably have sufficient stiffness or rigidity to be pushed through accumulated clot material within either tube without kinking or being caused to double back on itself. The guide member 119 may be coated with a friction-reducing material or non-stick material, for example PTFE, FEP, parylene, or silicone, in order to inhibit the adherence of clot material, thrombi or other obstructive debris, thus promoting better lumen clearance. The guide member 119 may be coated with a pharmacologic material. The guide member 119 may be coated with an anti-thrombogenic material. The guide member 119 may be coated with an anti-infective material. Alternatively, the guide member 119 may be coated with a combination of these. The guide member 119 also can have a guide lumen provided in fluid communication with one or more openings disposed through the wall of the clearance member 107 or with any or all of its individual branches 109 (not shown) as generally discussed in U.S. Pat. No. 7,951,243, which has already been incorporated by reference. The guide lumen and cooperating openings may be utilized to deliver flushing or irrigation fluid to assist in dislodging any material stuck to the clearance member 107 or its branches 109. In addition or alternatively, fluid expelled from the guide lumen through the one or more openings may be a solution provided to assist in the dislodgment, dissolution, and/or breakup of the debris. Fluids suitable for the particular purpose include, but are not limited to, anti-thrombolytic agents, Alkalol™, among others. In still other embodiments, such fluid may be or include a therapeutic agent such as but are not limited to antibiotic agents, anti-infective agents, anti-neoplastic agents, and other agents for a variety of purposes, including pain relief, treatment of infection, cancer, or to induce scarring (i.e. pleurodesis). Alternatively to delivering fluids, the guide lumen may be used to detect carbon dioxide in a patient's chest cavity as a means to determine whether there is a puncture in the patient's lung as generally discussed in the '243 patent.

As previously discussed, the clearance member 107 may be attached to or formed at the distal end of a guide member 119 that can be actuated from a proximal end of the medical tube; e.g. from outside the medical tube at or adjacent its proximal end. One embodiment of an actuation device is disclosed in the '243 patent incorporated above. Briefly, as disclosed in that patent a medical tube such as a chest tube can be connected at its proximal end to a shuttle-guide tube, and a shuttle translatable along the length of the guide tube can be magnetically coupled to a magnetic guide disposed within the guide tube. The magnetic guide is itself coupled to a proximal end (or in a proximal region) of the guide member such that translation of the shuttle along the guide tube length outside that tube induces a corresponding translation of the guide member within. Translation of the magnetic guide results in translation of the attached guide member and correspondingly of any clearance member at or adjacent its distal end to clear obstructive debris within the medical tube.

FIGS. 34-40 illustrate further embodiments of a device for actuating the guide member 119, and correspondingly clearance member 107, to clear obstructive debris in medical tubes according to any of the preceding embodiments. For example, referring first to FIG. 34, an actuation device includes a handle assembly 114 that is effective to translate the guide member 119, and therefore the clearance member 107, within the medical tube 102, e.g. a chest tube. In this embodiment the medical tube 102 can be coupled to the handle assembly 114 via a medical-tube fitting 115, which preferably has an internal diameter that is in continuity with the medical tube 102 at least at the point of attachment. The handle assembly 114 can also be connected to a vacuum drainage tube or other suction source (not shown) through a suction fitting 116 disposed at the proximal end of the handle assembly 114. The handle assembly 114 itself is substantially hollow or otherwise defines therein a conduit or passageway between the proximal and distal ends (i.e. between medical-tube and suction fittings 115 and 116, so that debris evacuated from the medical tube 102 can be drawn through the handle assembly 114 via a suction source. A guide member 119, e.g. according to any of the embodiments above described, is secured to or within the handle assembly 114 at or adjacent the member's 119 proximal end.

The length of the guide member 119 may be calibrated to ensure that the clearance member 107 at its distal end 108 does not extend out of or beyond the distal end 104 of the medical tube 102. For example, the length of the guide member 119 and its clearance member 107 together preferably substantially approximate the distance from the guide member's point of attachment with the handle assembly to just short of the distal end of the medical tube 102.

In this embodiment the medical tube 102 or at least a proximal portion thereof near or adjacent the handle assembly 114 is made of a flexible material that is elastically stretchable, such as a suitable elastomer or silicone. The medical tube 102 may be reinforced in this area for e.g. by coil reinforcement or other means such as braiding using metal or polymer wires or strands, to resist breakage and enhance elastic recoil. Alternatively, an intermediate, elastically stretchable tube can be interposed and connected in fluid communication between the handle member 114 and the medical tube 102 via suitable fittings (not shown). The intermediate tube may also be reinforced similarly as described above. In either case, preferably a thumb grip 117 is disposed on the outside of the medical tube 102 (or optionally on the aforementioned intermediate stretchable tube if present) at a location distally remote from the handle assembly 114.

In order to clear obstructing material from the medical tube 102, a user would grasp the medical tube 102 (or intermediate tube if present) at a position distal from the handle assembly 114, e.g. at the thumb grip 117, simultaneously grasp the handle assembly 114, and draw the handle assembly 114 proximally away from where the tube is being grasped with the other hand. As the effective length of the tubing between the handle assembly 114 and the distal end 104 of the medical tube 102 is increased when the medical (or intermediate) tube is stretched, a normally in-dwelling clearance member 107 (i.e. one that normally rests within the medical tube adjacent its distal end) will be drawn proximally through the medical tube. The clearance member 107 can thus clear debris in the lumen(s) served by the clearance member 107 or its branches 109 (if present) by drawing obstructive debris proximally, toward the handle assembly 114. While continuing to hold thumb grip 117 with one hand, the user can return handle assembly 114 back to its original location and the elastic portion of the medical tube 102 between thumb grip 117 and handle assembly 114 will shrink back to its original length, advancing the guide member 119 and clearance member 107 back to their original resting position. During this operation, care should be taken not to stretch the medical tube 102 (or its elastic portion) so far that the clearance member 107 becomes completely withdrawn from the partitioned region of the medical tube. This is because reinsertion of individual wires of the clearance member 107 into respective lumens in the partitioned region may be difficult as noted above. The user can repeat these steps to translate the clearance member 107 through the partitioned region of the medical tube 102, or a portion thereof, in order to dislodge blood, clots, and other debris that may have accumulated along the inner walls of the lumens in the partitioned medical tube. Loosened blood, clots, and other debris then can drain from the medical tube 102 through the fitting 115 into the handle assembly 114, and then through the fitting 116 to the vacuum drainage tubing and into a drainage receptacle (not shown). Suction is generally applied to the drainage receptacle to facilitate the drainage along this pathway.

FIG. 35 illustrates an exemplary multi-branch clearance member 107 having a plurality of branches 109 disposed in corresponding lumens within a multi-lumen distal region of a medical tube 102. Utilizing the stretchable tube/region feature described above, upon expanding the effective length of the tube the clearance member will be withdrawn from its resting position adjacent the distal end 108 of the medical tube, to a more proximal position relative to the distal end 108 as shown in FIG. 36. According to a preferred embodiment, the elasticity and length of the stretchable region/tube can be selected together so that the difference in its length between its relaxed state and fully-stretched state corresponds to the desired maximum degree of withdrawal of the clearance member 107 relative to the distal end of the medical tube 108. In this manner, for example, a multi-branched clearance member 107 can be assured not to be withdrawn entirely from the multi-lumen region of a medical tube 102 if the aforementioned length difference corresponds to or is just under the length of the multi-lumen region. In an alternative embodiment the multi-branch clearance member may be positioned in the tube so that it traverses only a portion of the partitioned region (having multiple lumens) in the medical tube when actuated. For example the distal end of the clearance member (i.e. of branches 109) may only traverse the distal and intermediate regions of the medical tube shown in FIG. 3 (corresponding to the cross-sections taken along lines A-A and B-B therein). Optionally they may be withdrawn only partially into the proximal region corresponding to the cross-section taken along line C-C. When the tube is stretched the clearance member clears the intermediate region, which is the most likely region for tube clogging to occur in the configuration shown in FIG. 3.

Figure 37:
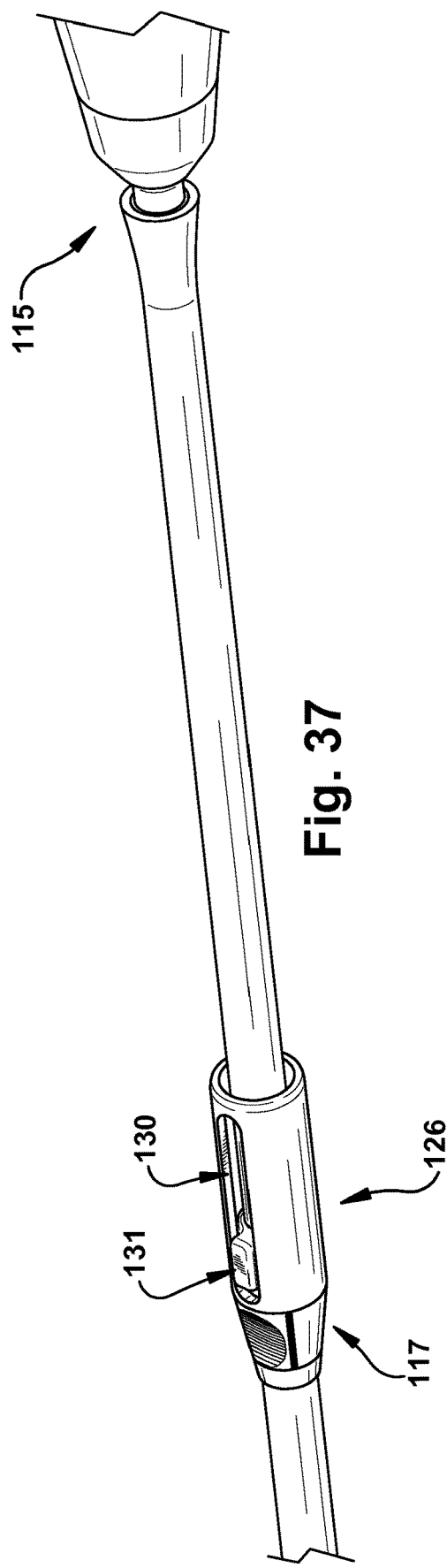
FIG. 37 is a close up perspective view of an embodiment of the thumb grip positioned along the medical tube of the embodiment illustrated in FIG. 34 as hereafter described.
Figure 38:
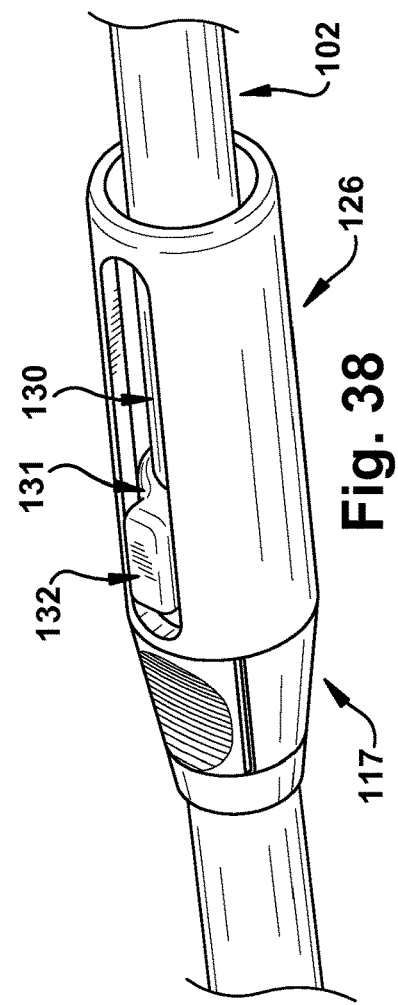
FIG. 38 is a close up perspective view of the thumb grip shown in FIG. 37 with a tab of a restraining element in a restraining portion of the thumb grip in a resting position.

In an alternative embodiment, a stretch-limiting mechanism can be incorporated to impede unintended complete withdrawal of the clearance member 107 from the partitioned region of the medical tube 102 if the medical tube 102 is stretched too far as mentioned above. FIG. 37 shows an embodiment of a clearance apparatus 101 similar to that of FIG. 34 wherein the thumb grip 117 is equipped with a stretch restraint portion 126. A distal end of the thumb grip 117 has an internal diameter that substantially corresponds to the outer diameter of the medical tube 102, thereby enabling securement of the grip 117, and correspondingly the restraint portion 126, to the medical tube 102 via an interference fit or via any other suitable mode of attachment; e.g. use of an adhesive. The medical tube 102 passes through a cylindrical passage in the stretch restraint portion 126 of the thumb grip 117 from its distal end, and continues to the handle assembly 114, where the medical tube 102 is coupled to the handle assembly 114. As shown in FIG. 38, a restraining element such as a ring 131 is housed within the restraint portion 126, and is slidably translatable therethrough along a longitudinal axis of the medical tube 102 that passes centrally through the center of the ring 131. The ring 131 has an internal diameter that substantially corresponds to, or that is even slightly smaller than, the outer diameter of the medical tube 102, thereby securing the ring 131 in place on the tube 102 via an interference fit. Alternatively or in addition, adhesives may also be used, for example when the restraining element is not configured as a ring that receives the tube 102 therethrough but is instead merely adhered to the surface of the tube 102. The ring 131 has an outer diameter substantially matching the inner diameter of the cylindrical passage within the stretch restraint portion of the thumb grip 117 for ease of alignment and translation therein. A tab or slide switch 132 is formed with or attached to an upper portion of the ring 131 and extends through a slot 130 provided in the housing of the restraint portion 126, aligned with its longitudinal axis. In its resting (unengaged) position, such as when the medical tube 102 or its elastically stretchable region is relaxed and unstretched, the restraining ring 131 is located near the distal end of the restraint portion 126, wherein the tab/switch 132 is disposed at the distal-most part of the slot 130. In its engaged position, the restraining ring 131 is located near the proximal end of the restraint portion 126, wherein the tab 132 is reaches and is engaged against the proximal-most part of the slot 130.

In use, as the medical tube 102 (or its elastic region) is stretched from the distally-located thumb grip 117 (as by separating the grip 117 and handle assembly 114), the tab 132 of the restraining ring 131, which is fixed on the medical tube, will approach and reach the proximal end of the slot 130. When the tab 132 reaches this point it will inhibit further stretching of the medical tube 114 thus inhibiting the clearance member 107 from being withdrawn from a partitioned region of the medical tube 102. At a minimum, the progression of the tab 132 toward the proximal end of slot 130 in use can serve as an indicator to the operator how far the tube has been stretched and, optionally, when to cease further stretching. In this embodiment, for example, the length of the slot could be calibrated to the length of a multi-lumen region of the medical tube 102 from which it is desired to prevent complete withdrawal of a clearance member 107 at the end of the guide member 119 within the tube. It can be appreciated that other mechanical means can be used to limit the stroke of the clearance member and prevent over stretching. In yet another embodiment, the clearance apparatus 101 may include one or a plurality of adjustable-length guide tubes coupled to or formed as part of the handle assembly 114 for the clearance apparatus 101, through which debris evacuated from the medical tube 102 may flow on its way to a suction source. Such adjustable-length guide tube(s) can be coupled, for example, in-line with and proximal to the medical tube with the guide member 119 extending at least partially therein, so that expansion and contraction of the adjustable-length guide tube can accommodate cycles of actuation (e.g. advancement and withdrawal) of the guide member 119 as already described. FIGS. 39 and 40 illustrate exemplary embodiments of handle assemblies 114 of clearance apparatus 101 having adjustable-length guide tubes associated therewith, in which the guide tubes are configured as accordion-style collapsible tubes.

Referring first to FIG. 39, a handle assembly 114 distal and proximal handle portions 120 and 121 that are longitudinally separable from one another. The handle portions 120 and 121 are connected via a proximal adjustable guide tube 122b that defines a substantially cylindrical and variable-length passageway therein, which in use will cooperate to partially define the sterile pathway between a medical tube and a suction source. As will be appreciated from FIG. 39, as the handle portions 120 and 121 are separated adjacent accordion elements in the tube 122b wall will unfold, thus lengthening the guide tube 122b. Conversely, as the handle portions 120 and 121 are brought together and ultimately attached to one another, the accordion elements will fold, thus collapsing the length of the tube 122b. The handle portions 120 and 121 can have respective and facing parking surfaces that cooperatively engage one another when the portions 120 and 121 are assembled to complete the handle assembly 114. For example, detent tabs, magnets or other reversible coupling structure can be used to secure the handle elements together when not in use.

A guide member 119 as above described can be disposed within the handle assembly 114, and be secured at its proximal end to the proximal handle element 121. In this manner, as the length of the adjustable guide tube 122b is increased by separating handle portions 120 and 121, a clearance member 107 at the distal end of the guide member 119 can be withdrawn from within a medical tube 102 as above described. Conversely, collapsing the guide tube 122b will advance the guide member 119 attached to the handle element 121 through the medical tube 102, e.g. to restore it to a resting or parked position adjacent the medical-tube distal end 108.

In addition to or instead of the proximal adjustable guide tube 122b, the clearance apparatus 101 can include a distal adjustable guide tube 122a as seen in FIG. 39. In the illustrated embodiment the distal adjustable guide tube 122a has accordion elements similarly as described above, and can be expanded and collapsed lengthwise in a similar manner; i.e. by adjusting the distance between the handle assembly 114 (or at least of the distal handle portion 120, and a fixed point along the length of the guide tube 122a, for example a fitting 115 for securing the distal end of the guide tube 122a to distal structure, such as a medical tube 102. Again, with the proximal end of the guide member 119 secured to the proximal handle portion 121, expansion of the distal guide tube 122a will result in withdrawal of the guide member and clearance member from the medical tube, whereas contraction of the guide tube 122a will result in advancement. Alternatively, and particularly when the proximal guide tube 122b is omitted as seen in FIG. 40, the proximal end of the guide member 119 can be secured within the distal handle portion 120; or in the handle assembly 114 if not separated into portions 120 and 121. case In an alternative embodiment, the guide member 119 may be actuated via a spool-drive mechanism as described in co-pending non-provisional patent application Ser. No. 14/624,161 filed on even date herewith, herein incorporated by reference in its entirety.

Although the invention has been described with respect to certain preferred embodiments, it is to be understood that the invention is not limited by the embodiments herein disclosed, which are exemplary and not limiting in nature, but is to include all modifications and adaptations thereto as would occur to the person having ordinary skill in the art upon reviewing the present disclosure, and as fall within the spirit and the scope of the invention as set forth in the appended claims.

What is claimed is:

1. An apparatus for clearing obstructions from a medical tube, comprising (i) a medical tube having a distal end, a proximal end, a lumen extending therebetween and defining a flow path through which fluids can flow from said distal end to and exit from said proximal end, and a multi-lumen region remote from the medical tube's proximal end, (ii) an elongate guide member extending at least partially within said lumen of said medical tube, and (iii) a branched clearance member comprising a plurality of individual branches each configured to be received within a respective lumen of the multi-lumen region, the clearance member extending at least partially within said medical tube and attached to or formed integrally with a distal end of said guide member and being configured to simultaneously clear obstructions in each of a plurality of distinct lumens in said multi-lumen region, said medical tube being coupled to a handle assembly located a predetermined distance from said distal end in a resting position thereof, wherein at least a portion of the medical tube along said flow path between said distal end and said proximal end thereof is composed of a flexible, elastic material, said portion of said medical tube being elastically stretchable from a relaxed, unstretched state to an elongated, stretched state by drawing the handle assembly from said resting position proximally away from said distal end of said medical tube, wherein said handle assembly returns to said resting position upon said portion of said medical tube elastically shrinking back to said relaxed, unstretched state from said elongated, stretched state, at least one of said plurality of distinct lumens having an associated, longitudinally-extending slot running parallel and in fluid communication therewith, wherein a respective branch of said clearance member is received and translates within said slot to correspondingly translate an associated clearance element within said at least one of the plurality of distinct lumens, wherein stretching said portion of said medical tube from the relaxed, unstretched state to the elongated, stretched state draws said clearance member proximally through said medical tube from an original resting position.

2. The apparatus of claim 1, each said branch of said clearance member having a respective clearance element disposed or formed at or adjacent its distal end, at least one of said clearance elements being configured to match a cross-sectional perimeter shape of the associated lumen in said medical tube.

3. The apparatus of claim 1, each of said plurality of distinct lumens having an associated, longitudinally-extending slot running parallel and in fluid communication therewith, wherein a respective branch of said clearance member is received and translates within the slot communicating with each of said distinct lumens to correspondingly translate an associated clearance element within the respective lumen.

4. The apparatus of claim 1, the medical tube having a partitioned region and one or a plurality of apertures through a wall of said medical tube in a distal region thereof, said clearance member being dimensioned and oriented so that it cannot pass through said apertures.

5. The apparatus of claim 1, said guide member being a guide wire, said clearance member being disposed at a distal end of said guide wire.

6. The apparatus of claim 1, a proximal end of said guide member being secured to said handle assembly.

7. The apparatus of claim 1, further comprising a thumb grip disposed on said medical tube at a location distally remote from the handle assembly, wherein said portion of said medical tube is stretched between said handle assembly and said thumb grip by separating them longitudinally relative to said medical tube.

8. The apparatus of claim 7, said thumb grip further comprising a stretch restraint portion.

9. The apparatus of claim 8, said stretch restraint portion comprising a restraining element secured to said medical tube and having a tab extending through a slot provided in a housing of said restraint portion, wherein stretching of said tube relative to said thumb grip causes said tab to translate proximally through said slot.

10. The apparatus of claim 9, wherein when said tab reaches and engages against a proximal portion of said slot, further stretching of said medical tube is thereby inhibited.

11. The apparatus of claim 9, said restraining element comprising a ring that surrounds said medical tube at a point of attachment thereto.

12. The apparatus of claim 1, wherein a length and elasticity of said medical tube are selected so that a difference in said tube's length between said relaxed state and a fully-stretched state of said portion thereof corresponds to a maximum degree of withdrawal of said guide member relative to the distal end of said medical tube.

13. The apparatus of claim 1, wherein said portion of said medical tube elastically shrinks back to said relaxed, unstretched state upon removal of an external force used to draw said handle assembly proximally away from said distal end of said medical tube.

14. The apparatus of claim 1, wherein shrinking of said portion of said medical tube back to the relaxed, unstretched state from the elongated, stretched state advances said clearance member distally through said medical tube to said original resting position.

15. The apparatus of claim 1, further comprising reinforcement means in the flexible, elastic material to further resist breakage and enhance elastic recoil.

16. The apparatus of claim 1, further comprising a coil reinforcement in the flexible, elastic material.

17. An apparatus for clearing obstructions from a medical tube, comprising a medical tube having a distal end, a proximal end, and a first lumen extending therebetween and defining a flow path through which fluids can flow from said distal end to and exit from said proximal end, said medical tube being coupled to a handle assembly located a predetermined distance from said distal end in a resting position thereof, and an elongate guide member extending at least partially within said lumen of said medical tube, wherein at least a portion of the medical tube along said flow path between said distal end and said proximal end thereof is composed of a flexible, elastic material, said portion of said medical tube being elastically stretchable from a relaxed, unstretched state to an elongated, stretched state by drawing the handle assembly from said resting position proximally away from said distal end of said medical tube, wherein said handle assembly returns to said resting position upon said portion of said medical tube elastically shrinking back to said relaxed, unstretched state from said elongated, stretched state, further comprising a thumb grip disposed on said medical tube at a location distally remote from the handle assembly, wherein said portion of said medical tube is stretched between said handle assembly and said thumb grip by separating them longitudinally relative to said medical tube, said thumb grip further comprising a stretch restraint portion, said stretch restraint portion comprising a restraining element secured to said medical tube and having a tab extending through a slot provided in a housing of said restraint portion, wherein stretching of said tube relative to said thumb grip causes said tab to translate proximally through said slot.

18. The apparatus of claim 17, wherein when said tab reaches and engages against a proximal portion of said slot, further stretching of said medical tube is thereby inhibited.

19. The apparatus of claim 17, said restraining element comprising a ring that surrounds said medical tube at a point of attachment thereto.

20. The apparatus of claim 17, the medical tube having a partitioned region and one or a plurality of apertures through a wall of said medical tube in a distal region thereof, said clearance member being dimensioned and oriented so that it cannot pass through said apertures.

21. The apparatus of claim 17, said guide member being a guide wire, said clearance member being disposed at a distal end of said guide wire.

22. The apparatus of claim 17, said medical tube having a proximal region and a distal region, and a second lumen extending in said distal region of said medical tube and separated from said first lumen by an interior wall of said medical tube, said second lumen being configured as a channel substantially open to a space outside said medical tube, said first and second lumens being in fluid communication via at least one opening in said interior wall.

23. The apparatus of claim 22, comprising a third lumen extending in said distal region and separated from said first lumen by at least one interior wall of said medical tube, said third lumen being configured as a channel substantially open to a space outside said medical tube and in fluid communication with said first lumen via at least one respective opening in said at least one interior wall.

\* \* \* \* \*